US008682952B2

(12) United States Patent
Kutzik et al.

(10) Patent No.: US 8,682,952 B2
(45) Date of Patent: Mar. 25, 2014

(54) SYSTEM FOR MAXIMIZING THE EFFECTIVENESS OF CARE GIVING

(75) Inventors: David Kutzik, Philadelphia, PA (US); Anthony P. Glascock, Philadelphia, PA (US)

(73) Assignee: Intel-GE Care Innovations LLC, Roseville, CA (US)

( * ) Notice: Subject to any disclaimer, the term of this patent is extended or adjusted under 35 U.S.C. 154(b) by 1415 days.

(21) Appl. No.: 11/763,102

(22) Filed: Jun. 14, 2007

(65) Prior Publication Data

US 2008/0084296 A1 Apr. 10, 2008

Related U.S. Application Data

(60) Continuation-in-part of application No. 11/081,988, filed on Mar. 16, 2005, now Pat. No. 7,937,461, and a division of application No. 09/710,569, filed on Nov. 9, 2000, now abandoned.

(51) Int. Cl.
G06F 15/16 (2006.01)

(52) U.S. Cl.
USPC .......... 709/200

(58) Field of Classification Search
USPC .......... 709/203, 217, 219, 220–224; 340/506; 379/38, 106.02
See application file for complete search history.

(56) References Cited

U.S. PATENT DOCUMENTS

| | | | |
|---|---|---|---|
| 3,955,184 | A | 5/1976 | Cinzori et al. |
| 4,058,678 | A | 11/1977 | Dunn et al. |
| 4,259,548 | A | 3/1981 | Fahey et al. |
| 4,319,228 | A | 3/1982 | Daniels |
| 4,418,333 | A | 11/1983 | Schwarzbach et al. |
| 4,563,780 | A | 1/1986 | Pollack et al. |
| 4,644,320 | A | 2/1987 | Carr et al. |
| 4,665,385 | A | 5/1987 | Henderson |
| 4,703,325 | A | 10/1987 | Chamberlin et al. |
| 4,706,689 | A | 11/1987 | Man |
| 4,803,625 | A | 2/1989 | Fu et al. |
| 4,831,242 | A | 5/1989 | Englehardt et al. |
| 4,864,519 | A | 9/1989 | Appleby et al. |
| 4,864,588 | A | 9/1989 | Simpson et al. |
| 4,924,211 | A | 5/1990 | Davies |

(Continued)

FOREIGN PATENT DOCUMENTS

| | | | |
|---|---|---|---|
| EP | 1 034 734 | A1 | 9/2000 |
| EP | 1034734 | A1 | 9/2000 |

(Continued)

OTHER PUBLICATIONS

International Search Report—PCT/US 2008/064-399 mailed on Sep. 15, 2008.

Primary Examiner — Jerry Dennison
(74) *Attorney, Agent, or Firm* — Pillsbury Winthrop Shaw Pittman LLP

(57) ABSTRACT

A method for determining the performance of a caregiver in a monitoring system for monitoring a user in a user living area the monitoring system including a remote monitoring site, including monitoring the user living area to detect an occurrence of an event to provide a detected event, providing event information representative of the detected event and determining a response of the caregiver to the detected event to provide caregiver response information. The event information and the caregiver response information are transmitted to the remote monitoring site.

18 Claims, 33 Drawing Sheets

(56) References Cited

U.S. PATENT DOCUMENTS

| | | | |
|---|---|---|---|
| 4,951,032 A | 8/1990 | Langsam | |
| 4,952,928 A | 8/1990 | Carroll et al. | |
| 4,964,065 A | 10/1990 | Hicks et al. | |
| 5,023,901 A | 6/1991 | Sloan et al. | |
| 5,045,839 A | 9/1991 | Ellis et al. | |
| 5,086,385 A | 2/1992 | Launey et al. | |
| 5,113,294 A | 5/1992 | Kim | |
| 5,122,976 A | 6/1992 | Bellows et al. | |
| 5,127,045 A | 6/1992 | Cragun et al. | |
| 5,204,670 A | 4/1993 | Stinton | |
| 5,228,449 A | 7/1993 | Christ et al. | |
| 5,235,527 A | 8/1993 | Ogawa et al. | |
| 5,266,944 A | 11/1993 | Carroll et al. | |
| 5,267,174 A | 11/1993 | Kaufman et al. | |
| 5,311,185 A | 5/1994 | Hochstein et al. | |
| 5,361,265 A | 11/1994 | Weinberger et al. | |
| 5,400,246 A | 3/1995 | Wilson et al. | |
| 5,410,471 A | 4/1995 | Alyfuku et al. | |
| 5,441,047 A | 8/1995 | David et al. | |
| 5,539,665 A | 7/1996 | Lamming et al. | |
| 5,546,580 A * | 8/1996 | Seliger et al. | 1/1 |
| 5,557,514 A | 9/1996 | Seare et al. | |
| 5,650,940 A | 7/1997 | Tonozuka et al. | |
| 5,692,215 A | 11/1997 | Kutzik et al. | |
| 6,002,994 A | 12/1999 | Lane et al. | |
| 6,108,685 A | 8/2000 | Kutzik et al. | |
| 6,154,726 A | 11/2000 | Rensimer et al. | |
| 6,230,142 B1 | 5/2001 | Benigno et al. | |
| 6,381,576 B1 | 4/2002 | Gilbert | |
| 6,640,212 B1 | 10/2003 | Rosse | |
| 6,804,656 B1 * | 10/2004 | Rosenfeld et al. | 705/3 |
| 7,091,865 B2 | 8/2006 | Cuddihy et al. | |
| 7,107,106 B2 | 9/2006 | Engleson et al. | |
| 2004/0249670 A1 | 12/2004 | Noguchi et al. | |
| 2005/1031740 | 6/2005 | Massenzio et al. | |
| 2005/0209881 A1 | 9/2005 | Norton | |
| 2005/0278409 A1 | 12/2005 | Kutzik et al. | |
| 2006/0071797 A1 | 4/2006 | Rosenfeld et al. | |
| 2007/0043590 A1 | 2/2007 | Lee | |
| 2009/0204642 A1 * | 8/2009 | Gliklich | 707/104.1 |

FOREIGN PATENT DOCUMENTS

| | | |
|---|---|---|
| EP | 1 071 055 A1 | 1/2001 |
| EP | 1071055 A1 | 1/2001 |
| WO | 2006060806 A2 | 6/2006 |

* cited by examiner

Client Summary Page
Alerts

| | |
|---|---|
| Client Number | All Clients |
| Caregiver(s) | 'CG-1' 'CG-2' |
| Month Reviewed | March 2007 |

Number of alerts for March 2007: 110

| | |
|---|---|
| 1. Activity | 16 |
| 2. Fall | 1 |
| 3. Meals | 33 |
| 4. Overnight | 18 |
| 5. Temperature | 20 |
| 6. Wake-up | 20 |

Alert Trends for 6 months through March 2007:

Client Summary Page
TAOs

Client Number: All Clients

Caregiver(s): 'CG-1' 'CG-2'

Month Reviewed: March 2007

Number of TAOs for March 2007: 26

TAO Alert Details:

1. Wake-up 3
2. Overnight 8
3. Fall 2
4. Meals 14
5. Temperature 3
6. Activity 3
7. Base Station 3

TAO Trends through March 2007:

TAO Summary 03/28/2007

1) 99 TAOs since 2006-09-10;
2) 11 clients have had one or more TAOs:

| **Client ID** | **Total** |
|---|---|
| X-01 | 4 |
| X-02 | 12 |
| X-03 | 23 |
| X-04 | 29 |
| X-05 | 1 |
| X-06 | 3 |
| X-07 | 4 |
| X-08 | 3 |
| X-09 | 6 |
| X-10 | 3 |
| X-11 | 11 |

3) Distribution of Responses/Alerts:

| **Responses** | **Alerts** |
|---|---|
| Wake-up: 12 | Activity: 28 |
| Meals: 54 | Fall: 4 |
| Falls: 3 | Meals: 124 |
| Activity: 12 | Overnight: 55 |
| Overnight: 23 | Temperature: 97 |
| Base Station: 8 | Wake-up: 48 |
| Temperature: 11 | |

4) Actions:
   - Other Actions: 64
   - Phoned Client: 46
   - Spoke to care professional: 44
   - Visited client in home: 23
   - Spoke to client face to face: 20
   - Phoned client no answer: 18
   - Other contacts: 14
   - Spoke to informal support: 11
   - No Action Taken: 3

4) TAOs by Caregiver:
   - CG-1: 86
   - CG-2: 13

*FIG. 15*

Summary Narrative Report

2007-03-01 through 2007-03-28 10:32:33

FIG. 16A

| Date | Client (TAO Id) | Caregiver | Alert | Action | Outcome |
|---|---|---|---|---|---|
| 03/02/07 | X-02 | CG-1 | -Meals | -Spoke to client face to face<br>-Visited client<br>-Other action taken: Visit client as I was schedule to visit. Client said all was fine. Client seems the normal way. | -Other outcome: Client is at home (03/02 09:21) Encouraged client to eat and explained the importance. We will monitor and encourage food intake. |
| 03/02/07 | X-10 | CG-1 | -Overnight | -Phoned client<br>-Other action taken: Phone client who answered that there was no problem at this time. | -Other outcome: Client was at home (03/02 09:26) Client answered that all was ok,encouraged fluid intake. We will monitor clients behaviour. |
| 03/02/07 | X-09 | CG-1 | -Temperature | -Phoned client<br>-Spoke to care professional Care Co-ordinator<br>-Other action taken: Spoke to client who replied that the room felt ok. Encouraged to wear warm clothing. Spoke to the Care Co-ordinator about it. | -Other outcome: Client was at home (03/02 09:38) The temperature seems to be low in the mornings. Informed the Care Co-ordinator who will visit and will check on the heating. |
| 03/07/07 | X-08 | CG-1 | -Meals | -Phoned client<br>-Other action taken: Spoke to client who replied that all was fine, encouraged to eat and will check that client is fine. | -Other outcome: Client is at home (03/07 09:11) Client explained that there is no worry at this time and agreed to eat at every meal time. I will monitor client's well being. |

FIG. 16B

| | | | | | |
|---|---|---|---|---|---|
| 03/07/07 | X-05 | CG-2 | -Meals | -Phoned client<br>-Spoke to care professional Care Co-ordinator<br>-Other action taken: Phoned client to ask about meals, client replied that all is fine and have eaten when feeling hungry. Encouraged to eat. | -Other outcome: Client was at home (03/07 09:28) Client was very clear that all was fine and no need to worry. Encouraged to eat and informed the Care Co-ordinator. |
| 03/09/07 | X-05 | CG-2 | -Meals | -Spoke to care professional Support Worker<br>-Other action taken: Spoke to Support Staff who was with client yesterday, Staff said client has a sore mouth which could be the cause of not attending meals well. | -Other outcome: Client is at home (03/09 10:48) Client is eating much better today but still not very comfortable. Support Worker introduced soft food to client when visited. We will monitor the problem. |
| 03/12/07 | X-05 | CG-1 | -Meals | -Spoke to care professional Support Worker<br>-Other action taken: Spoke to Support Staff as client wouldn't be able to remember what happened the day before. Staff said client has a sore mouth and wasn't able to eat properly. | -Other outcome: Client was at home (03/12 12:23) Client was given soft food and fluid at that time. Support Workers were very observant and have made a report on this. |
| 03/15/07 | X-05 | CG-2 | -Meals<br>-Activity | -Phoned client no answer<br>-Spoke to care professional Care Co-ordinator<br>-Other action taken: Phoned client got no answer, spoke to Care Co-ordinator who said that client went to the Day Center, informed of the alert. | -Other outcome: Client was at the Day Center (03/14 09:41) Client had switched the system off the day before and it wasn't switched on until the client arrived home from the Day Center. Client has been monitored for any changes. |

FIG. 16C

| | | | | | |
|---|---|---|---|---|---|
| 03/15/07 | X-05 | CG-2 | -Overnight<br>-Activity | -Phoned client<br>-Spoke to care professional Support Worker<br>-Other action taken: Spoke to client who replied that all was fine. Spoke to Support Worker who was visiting client and informed of the alert. | -Other outcome: Client was at home (03/15 10:26) Client seems fine at this time and Support Staff are being observant. |
| 03/21/07 | X-06 | CG-1 | -Overnight | -Spoke to informal support Relative<br>-Spoke to care professional Care Co-ordinator (CPN)<br>-Contacted other person, Warden<br>-Other action taken: Client has been unstable recently due to increased wandering. Daughter will be accompanying her to the GP and Care Co-ordinator has arranged a CPA to discuss future plans to meet her deteriorating mental state. | -Assisted Living<br>-Other outcome: CPA (03/21 07:18) Arrangements are being made for the Care Programming Team to meet and discuss the care package which will include placement into residential home. |

HELPING HANDS HOME CARE

Care Tracking Report

3/1/07 to 3/31/07

| Care Worker | Alert Days | Response Percent | Care Plan Change | Pay Attention |
|---|---|---|---|---|
| Sarah | 57 | 97 | Yes | |
| Rolanda | 44 | 100 | No | |
| Jenna | 23 | 100 | No | |
| Barbara | 39 | 56 | No | |
| Joseph | 51 | 96 | Yes | ← Pay Attention |
| Ronnie | 20 | 90 | No | |
| Pat | 36 | 92 | No | |
| William | 61 | 100 | No | |
| Jackie | 54 | 100 | No | |
| Peter | 63 | 87 | No | ← Pay Attention |

Click on name for details → *(clicked on Barbara Frost...)*

*FIG. 17A*

HELPING HANDS HOME CARE

Second Page: Shows information on a single care worker as a table and text.

| Care Worker | Total Number of Clients | Number of Monitored Clients | Number of Alert Days | Number of Responses | Number of Billable Interventions |
|---|---|---|---|---|---|
| Barbara | 24 | 16 | 39 | 22 | 12 |

Case Load for Barbara Frost

| Client | Alert Days | Response Days | Care Plan Coverage | Billable Services | Intervention/ Outcome |
|---|---|---|---|---|---|
| Sarah | 0 | 0 | | | |
| Jane | 4 | 0 | | | Yes |
| Jennie | 1 | 1 | | | |
| Liz | 0 | 0 | | | |
| Mack | 9 | 6 | Yes | increase | Yes |
| Bela | 0 | 0 | | | |
| Betty | 3 | 3 | | | Yes |
| Pam | 4 | 3 | | | |
| Lewis | 3 | 2 | | decrease | |
| Meg | 0 | 0 | | | |
| Lucy | 1 | 1 | | | |
| Sharon | 7 | 3 | Yes | increase | |
| Bob | 3 | 3 | | | |

*FIG. 17B*

HELPING HANDS HOME CARE

Third Page: History of care delivery for a single care worker.

Text:
Note decline in responses per alert over two months. Pay attention to individual clients Mack and Sharon who have had the largest decline.

Individual Wellbeing Record
March 15, 2007
for: Samuel

> • Pay attention to:

Meal Activities 3/15/07.
Lower than expected meal activities

Bathroom Usage 3/15/07.
Higher than expected overnight bathroom usage.

> Action Taken:

3/15/07      11:21am.
             Visited client.

3/15/07      1:33pm.
             Spoke with client's daughter.

3/15/07      3:10pm.
             Phoned visiting nurse.

CLICK FOR DETAILS ⟶ ○

Individual Wellbeing Record

Six Month Trend Page for Samuel

Care Plan Changes:
12/13/07 Increased HHA hours.
10/19/07 Physical therapy ended.

CLICK FOR DETAILS → ○

SYSTEM FOR MAXIMIZING THE EFFECTIVENESS OF CARE GIVING

CROSS-REFERENCE TO RELATED APPLICATIONS

This application is a continuation-in-part of U.S. patent application Ser. No. 11/081,988, filed Mar. 16, 2005 (which issued as U.S. Pat. No. 7,937,461 on May 3, 2011), and a divisional of U.S. patent application Ser. No. 09/710,569, filed Nov. 9, 2000 (which has been abandoned).

BACKGROUND OF THE INVENTION

1. Field of Invention

This invention relates to a system for providing remote monitoring and intervention to maintaining independent living.

2. Description of Related Art

All references cited herein are incorporated herein by reference in their entireties.

BRIEF SUMMARY OF THE INVENTION

A method for determining the performance of a caregiver in a monitoring system for monitoring a user in a user living area the monitoring system including a remote monitoring site, including monitoring the user living area to detect an occurrence of an event to provide a detected event, providing event information representative of the detected event and determining a response of the caregiver to the detected event to provide caregiver response information. The event information and the caregiver response information are transmitted to the remote monitoring site.

BRIEF DESCRIPTION OF SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 15 shows a TAO summary according to the present invention.

FIGS. 16A-C show further TAOs according to the present invention.

FIGS. 17A-C show a care tracking report according to the present invention.

DETAILED DESCRIPTION OF THE INVENTION

Figure 1:
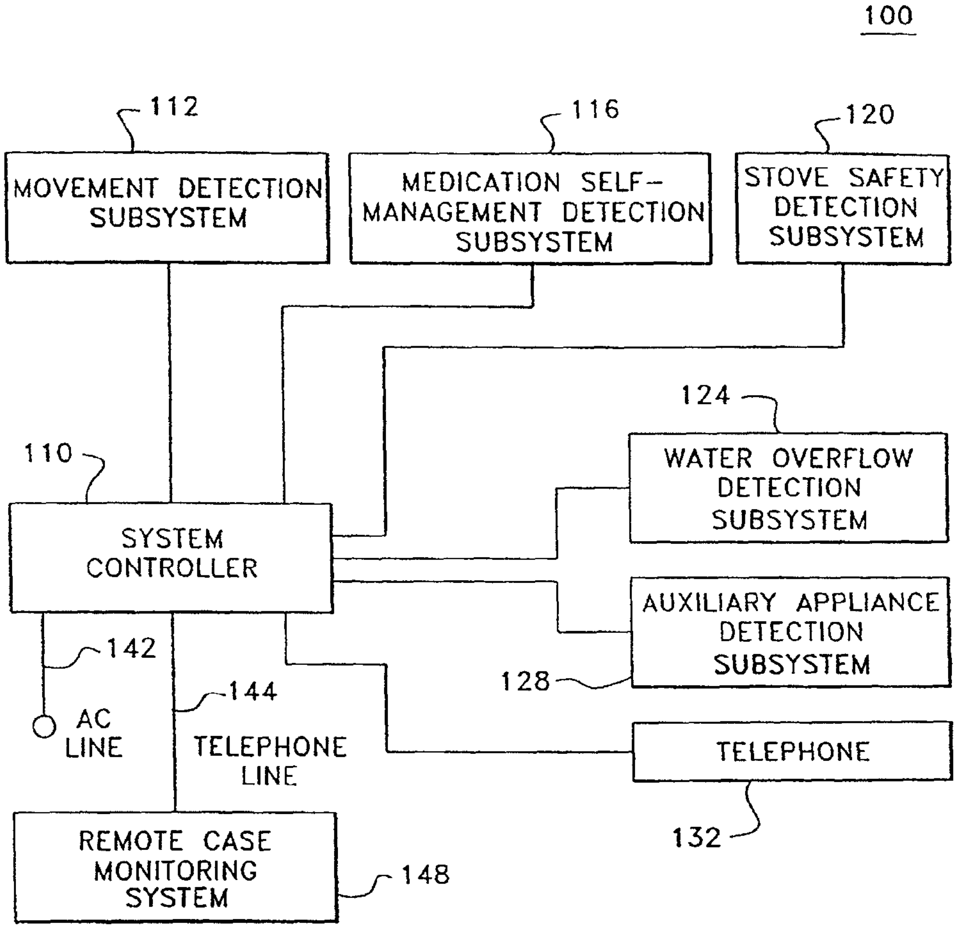
FIG. 1 is a block diagram representation of the user monitoring system of the present invention.

Several known user monitoring systems have an immediate response feature. In one prior art system if a user falls down and is unable to get up the user may push a button on a small radio frequency transmitter. This radio frequency transmitter may be worn by the user. For example, it may be worn on a necklace or on a key chain for convenience and to assure that it is available when it is needed. Pushing the button activates a device at the residence of the user which places a telephone call to a user remote monitoring site. Personnel at the remote monitoring site may listen and talk through a paging telephone in order to communicate with the user. Additionally, personnel at the user monitoring site may dispatch an ambulance or other assistance for the user.

There is a large number of devices designed to enhance medication compliance and to monitor the extent of noncompliance. Devices available in the prior art include timers, medicament containers and combinations of timers and containers. Also available in the prior art are multiple compartment timed containers which only open at timed intervals and beep until the compartment is opened and closed. Devices available to researchers include specialized containers and bottle caps which record the date and time of opening of the container. This information is provided in a machine transferable form which may be applied to a computer for analysis of scheduling and dosing compliance.

In addition, a variety of specialized dispensers using stripped, bubble wrapped medicaments is available. These dispensers are available from pharmacists and are adapted to provide the correct pills at scheduled times and use a less expensive method for loading doses than other prior art self-loading timed dispensers. One prior art system in particular uses a host computer system to control a dispensing schedule in addition to a local timer-memory system. Another system uses color coded indicia to aid in identification of medication by users.

Various home health monitoring systems are also known in the prior art. These systems fall into a broad category of devices which offer in-home electronic monitoring of health conditions ranging from fetal heart beat to blood pressure and blood sugar. Some of these health monitoring systems transmit a log to a central unit if a monitored parameter is outside a predetermined range. Other systems monitor predetermined health related parameters in the environment of the user.

The present invention comprises a user monitoring system for monitoring and intervening in selected activities of daily living for users requiring differing levels of monitoring or supervision. The user monitoring system monitors and provides interventions relating to four principal event domains. These event domains are (1) movement around the home, (2) medication compliance by the user, (3) problems with usage of stoves or other potentially dangerous appliances, and (4) selected auxiliary appliance control. Each of these event domains corresponds to a detection subsystem of the user monitoring system. Each detection subsystem is linked to the user monitoring system by means of radio frequency signals transmitted from subsystem sensors and received by a system controller device within the user monitoring system. In addition to using information obtained by monitoring the selected activities of daily living to make decisions locally, the user monitoring system produces, stores and transfers data concerning all monitored event domains and intervention activity to a remote case management system for further analysis and intervention. The remote case management monitoring system may use a knowledge base and an inference generator in order to make decisions regarding various types and degrees of intervention. The user monitoring system may provide reminders for the user to take their medications. Local and remote reprogramming of event parameters determining interventions and data recording are provided. The user monitoring system may execute controlled shutdown of the stove and other appliances as well as call the remote monitoring site in the event of possible emergencies. Data for monthly case monitoring reports which may include event logs of problem occurrences may be provided to permit cross-sectional and long-term trend analysis of difficulties. These may serve as a basis for case management decisions determining additional contacts and interventions.

The invention will be illustrated in more detail with reference to the following Examples, but it should be understood that the present invention is not deemed to be limited thereto.

DETAILED DESCRIPTION OF PREFERRED EMBODIMENTS

Referring to the drawings, wherein the same reference numerals are used to designate the same elements throughout, there is shown in FIG. 1 a block diagram representation of a user monitoring system 100 in accordance with a preferred embodiment of the present invention. The monitoring system may be used to monitor and assist elderly persons, functionally impaired persons or the like on a temporary short-term basis or on a long-term basis. The user monitoring system 100 includes a microprocessor based system controller device 110 linked to various sensors which are provided within a number of activity detection subsystems 112-128. Activity detection subsystems 112-123 are adapted to monitor various activities of daily living of the user of the monitoring system 100. Also included are the in-home telephone 132 which is located within the user living area being monitored and an outside telephone line 144.

Any number of daily living activity detection subsystems may be provided within the user monitoring system 100 of the present invention. The detection subsystems provided in one embodiment may include a movement detection subsystem 112, a medication self-management detection subsystem 116, and a stove safety detection subsystem 120. However, it will be understood that using differing types of monitors, any other activities of daily living may be sensed and detected within user monitoring system 100. Additionally, the user monitoring system 100 may be coupled to a computer based case monitoring system 148 by way of a telephone line 144. Formal and informal care givers may be provided with information to determine whether short and long term intervention is required using the data transmitted to the case monitoring system 148. It will be understood that in addition to telephone line 144 or interactive television, any method of transmitting messages to system 148 may be used. For example, messages may be transmitted by an add-on fiber optic cable box or a portable transmitter.

The user monitoring system 100 integrates sensor data from different activity domains to make a number of determinations at predetermined times on a twenty-four hour basis. One activity domain determination within the user monitoring system 100 includes movement of the person being monitored. In this movement domain determinations are made by the movement detection subsystem 112 whether the user is up and around. The detection information which results from this determination by movement detection subsystem 112 is transmitted to the system controller device 110.

Another activity domain determination within the user monitoring system 100 is a determination of medication self-management. In this activity domain determinations are made whether the user is following a predetermined medication regimen. This determination is made by the medication self-management detection subsystem 116 of the user monitoring system 100. The detection information which results of this determination by medication self-management system 116 is also transmitted to the system controller device 110.

Stove usage is another activity domain which is monitored by the user monitoring system 100. In this activity domain determinations are made as to whether a stove has been left on inappropriately. Detection information in accordance with this determination is transmitted to the system controller device 110. This determination may be made by differing embodiments of the stove safety detection subsystem 120 depending on whether the stove being monitored by detection subsystem 120 is a gas stove or an electric stove.

In the preferred embodiment of the user monitoring system 100 it is also possible to monitor and control other designated appliances using one or more auxiliary systems subsystems 128. These auxiliary systems may include, for example, other potentially harmful appliances such as irons or electric space heaters. System controller device 110 also receives detection information representative of the determination of the detection subsystems 116, 128.

Figure 2:
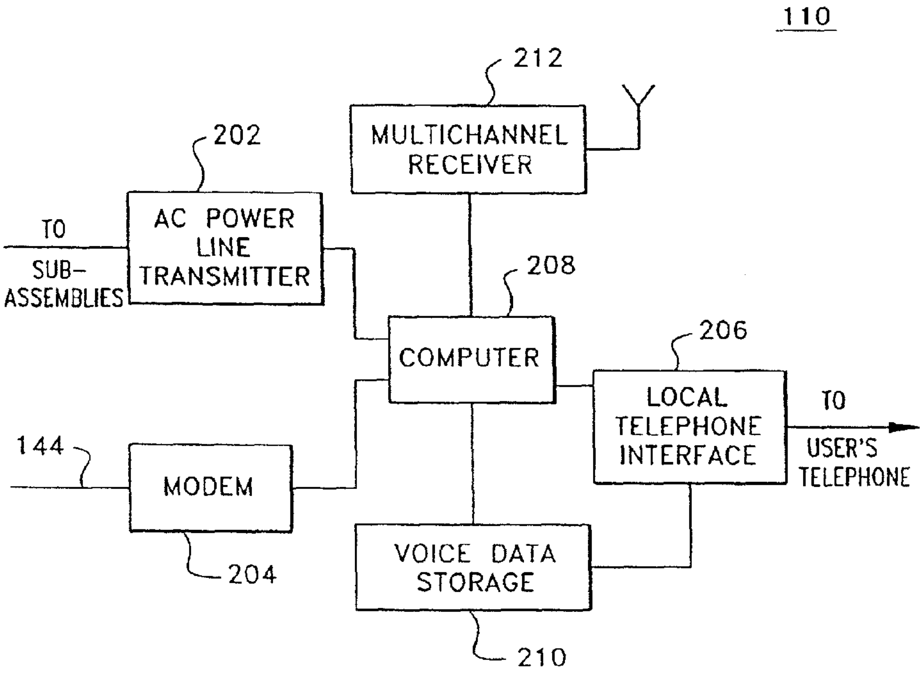
FIG. 2 is a more detailed block diagram representation of the system controller device of FIG. 1.

Referring to FIG. 2, there is shown a more detailed block diagram representation of the system controller device 110 of the user monitoring system 100. The system controller device 110 includes a computer 208 and a radio frequency multichannel receiver 212. The computer 208 may be any type of computer capable of running C++ or any similar functionally equivalent object code. The various channels of the radio frequency receiver 212 are provided within system controller device 110 for receiving radio frequency signals transmitted from the various detection subsystems 112-128 by way of detection system antennas provided within the various detection subsystems 112-128. It will be understood that a sufficient number of information channels required to accommodate the number of detectors should be provided within system 100. These communication channels may be provided, for example, by a number of radio frequency channels within radio frequency receiver 212.

The various channels of the radio frequency receiver 212 thus serve as detection information channels for receiving detection information within the monitoring system 100. However, it will be understood that any information channel or information conduit or means for applying information may be used to apply information from detection subsystems 112-128 to system controller 110. The system controller device 110 is also provided with an AC power line transmitter 202 for applying control signals to the various detection subsystems 112-128 and to the remote monitoring site 148. Additionally, a system controller modem 204, and a telephone interfacing circuit 202 are present within the system controller 110.

In the preferred embodiment of the user monitoring system 100 the system controller device 110 may also be provided with a voice data storage device 210. The voice data storage device 210 may be used within the user monitoring system 100 to store various audio reminder and inquiry messages which may be provided to the user being monitored at predetermined times.

The power supply of the system controller device 110 of the user monitoring system 100 may include a well regulated battery with a battery backup to prevent loss of valuable user data stored in the user monitoring system 100. The radio frequency multichannel receiver 212 of the system controller device 110 is a conventional multichannel radio frequency device having appropriate anti-interference technology for preventing interference between the various subsystem channels and interference from external sources. The anti-interference technology may be, for example, broad spectrum modulation.

In the preferred embodiment of the system controller device 110 the radio frequency receiver 212 may be a pulsed radio frequency device. The power line transmitter 202 of the system controller device 110 is a conventional system for turning controlled appliances on and off. In the preferred embodiment of the user monitoring system 100, this control may be accomplished by sending pulsed radio frequency signals through the AC lines of the living areas of the user as understood by those skilled in the art. The use of different pulsed signals, decodable by different detection subsystems, is effective to provide any required number of control information channels for applying control signals to detection subsystems 112-128 by system controller 110. However, it will be understood that the transmission of control information from the system controller device 110 to the various detection subsystems 112-128 may be performed by any suitable information channels.

The controller modem 204 of the system controller device 110 may be a conventional modem capable of providing known incoming and outgoing modem protocols. The outgoing protocols of the controller modem 204 may be used for data transfer from the system controller device 110 to the case monitoring site 148 or to other locations by way of telephone line 144. The incoming protocols of the system controller modem 204 may be used for reprogramming various monitoring and intervention parameters of the user monitoring system 100. Reprogramming may be performed either by the remote case monitoring site 148 through the controller modem 204 or directly to the system controller device 110. Additionally, the incoming protocols may be used for any type of communication with the user monitoring system 100.

The local telephone interface circuit 206 of the system controller device 110 provides several functions within the user monitoring system 100. It transmits incoming calls received by the user monitoring system 100 by way of the telephone line 144 to the in-home telephone 132. The telephone interface device 206 also connects ringing voltage as well as synthesized voice messages from the voice data storage device 210 to the in-house telephone 132 on command to provide messages to the user by way of the in-home telephone 132. It also makes several determinations regarding the state of the in-house telephone 132. For example, determinations when the in-home telephone 132 is off-hook, when the in-home telephone 132 is not off-hook, and whether the number one has been pressed on the in-home telephone 132 may be made by the local telephone interface circuit 206.

The user monitoring system 100 operates in a home mode and in an away mode. The away mode of the user monitoring system 100 may be selected by pressing a dedicated away switch (not shown) located in a convenient location in the home of the user. Additionally, the away mode of user monitoring system 100 may be remotely set from the case management monitoring host site 148. The home mode of the user monitoring system 100 may be passively set, for example, by the opening of a door when the user returns home.

In the preferred embodiment of the system controller device 110, a reprogrammable microprocessor receives detection information, makes determinations as set forth herein, and provides control information accordingly. However, it will be understood by those skilled in the art that any type of control circuitry capable of performing the operations set forth herein may be used within the user monitoring system 100.

Figure 3:
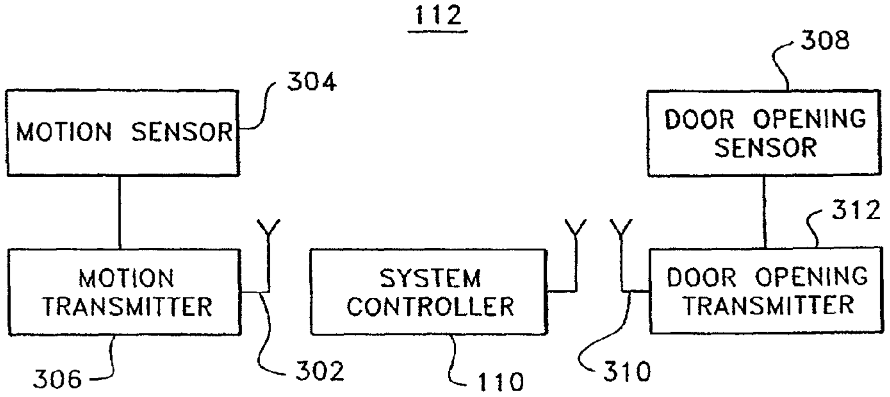
FIG. 3 is a block diagram representation of the movement activity detection subsystem of the user monitoring system of FIG. 1.

Referring to FIG. 3, there is shown a block diagram representation of a preferred embodiment of the movement activity detection subsystem 112 of the user monitoring system 100. Within the user monitoring system 100, movement sensed by the movement activity detection subsystem 112 is assumed to indicate that the user being monitored is up and around.

It will be understood by those skilled in the art that the configuration of the movement detection subsystem 112 may vary according to the differing living areas being monitored by user monitoring system 100. However, in general the movement detection subsystem 112 includes at least one and preferably several motion sensors such as motion sensor 304 positioned at spaced locations within the home of the user or a conventional reed switch door opening such as sensor detector 308. The motion sensor 304 and the reed switch 308 are provided for determining whether there is movement or activity within the living area being monitored by the user monitoring system 100.

In the most basic embodiment of the detection subsystem 112, only a single motion sensor 304 may be provided. In this case the single motion sensor 304 is preferably placed between the bed of the user and the bathroom. In a case where only a single reed switch is provided within the movement detection subsystem 112, it is preferably placed on the door of the bathroom. Such basic configurations of the movement detection subsystem 116 are effective to determine whether the user being monitored has gotten out of bed or has gone to the bathroom after a predetermined time.

When an activity is sensed by the motion sensor 304 or the door opening sensor 308, a motion transmitter 306 of the motion detection subsystem 112 transmits a radio frequency signal by way of the motion antenna 302. This motion signal representing an activity of daily living by the user is received by the system controller device 110 of the user monitoring system 100. It is therefore activity of daily living information which indicates that the detected user movement has occurred within the home being monitored by the user monitoring system 100.

Similarly, a conventional reed switch (not shown) or other type of switch within the door opening sensor 308 is provided with a radio frequency door opening transmitter 312. The door opening transmitter 312 transmits a door opening signal indicating the opening of a door or cabinet to which the sensor 308 is applied. The door opening signal is transmitted by detection subsystem 112 is a radio frequency signal representative of this activity. It is transmitted to the system controller device 110 by way of the motion detection antenna 310.

If the dwelling being monitored is large or complex a more elaborate configuration of movement and activity sensors 304, 308 may be required within the movement detection subsystem 112 of the user monitoring system 100. However, in the preferred embodiment of the user monitoring system 100 at least movement from the bed and movement into and out of the bathroom should be monitored by the movement detection subsystem 112. Inappropriate periods of user inactivity as indicated by sensors 304, 308 or other sensor disposed in these locations may indicate a medical emergency. It will be understood that a plurality of motion sensors or switches such as reed switches may be placed in locations within the living area being monitored and that there are no theoretical limitations in the number of such devices which may be used with the movement detection system 112.

When the movement detection subsystem 112 operates in the home mode the user monitoring system 100 is in a twenty-four hour cycle. This twenty-four hour cycle includes information with respect to the usual waking time of the user being monitored. Using the motion sensors 304, 308 of the motion detection subsystem 112 the user monitoring system 100 determines if the user remains in bed a specified length of time beyond the usual waking time or has not gone from the bed to the bathroom for a predetermined time period. If the user monitoring system 100 determines an abnormal lack of user activity such as this it may enter a wake up monitor phase.

In the wake up monitor phase of the user monitoring system 100 the system controller device 110 may place a telephone call to the user by way of the telephone 132 in order to determine whether the user is having a problem. If the telephone call placed by the system controller device 110 is answered, the user is prompted by the system controller device 110 to depress a predetermined key on the in-home telephone 132. For example, the user may be prompted to press the telephone key indicating the number one. If the user complies with the prompt from the system controller device 110 the wake up monitor phase of the user monitoring system 100 is complete. If there is no answer to the call placed by the system controller device 110 and the user monitoring system 100 is not in away mode, or if the user answers the telephone but does not depress the requested key, the user monitoring system 100 contacts the case monitoring site 148 with an immediate status report indicating a potential problem with the user.

Assuming all is well, the activity movement detection subsystem 112 of the user monitoring system 100 merely monitors all system status changes within system 100. This includes monitoring and storing information from the motion detectors 304, 308 representing movement and the opening and closing of doors, the usage of medication, the usage of the stove and appliances, and any other auxiliary devices which maybe monitored by the user monitoring system 100.

Each status change detected by the user monitoring system 100 is assumed to indicate activity of the user being monitored. In the event of the detection of a period of inactivity in excess of a predetermined amount of time during the usual waking hours of the user, the user monitoring system 100 returns to the wake up monitor phase and places a telephone call to the user as previously described. The period of inactivity required for the user monitoring system 100 to return to the wake up monitor phase is adjustable depending upon the habits of a particular user but may, for example, be two and one-half hours.

When the user monitoring system 100 is in the away mode it does not record or report any activities. It merely waits for active or passive resetting of the home mode as previously described Active resetting of the home mode of the user monitoring system 100 occurs when the user activates a dedicated home/away switch which may be mounted at any convenient location. Passive resetting of the mode of the user monitoring system 100 may occur when the user returns and changes the status of any detection subsystem 112-128.

Figures 4A, 4B:
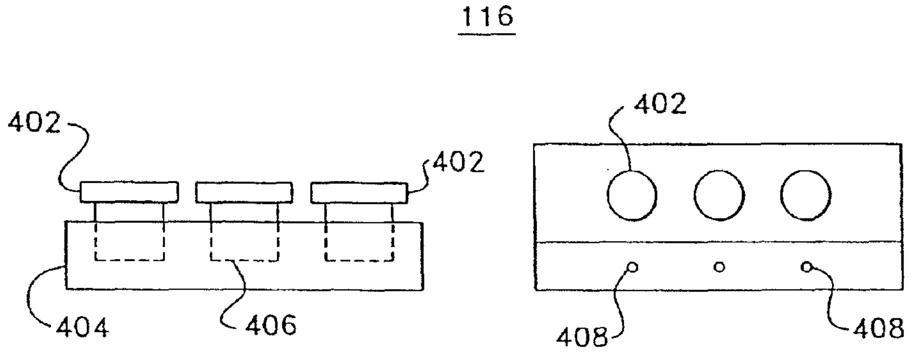
FIGS. 4A, B are side and top plan views of the medication self-management detection subsystem of the user monitoring system of FIG. 1.
Figure 5:
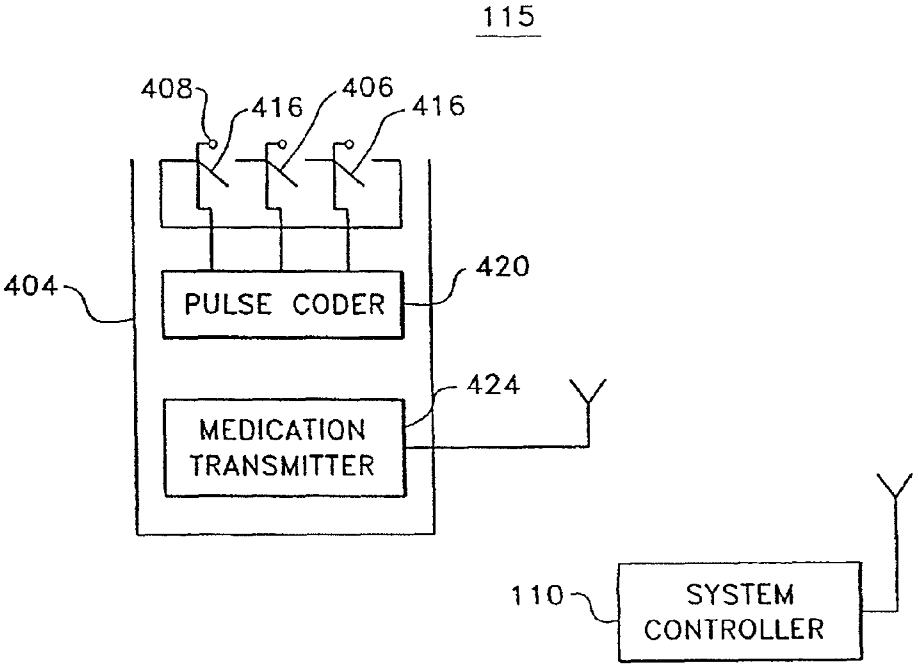
FIG. 5 is a more detailed block diagram representation of the medication self-management detection subsystem of FIGS. 4A, B.

Referring to FIGS. 4A, B, and 5, there are shown a side view, a top plan view, and a schematic representation of a preferred embodiment of the medication self-management detection subsystem 116 of the user monitoring system 100 of the present invention. The medication self-management detection subsystem 116 comprises a medication holder 404 which is a specialized portable holder or caddy for holding at least one medication container 402 in a corresponding container opening 404.

In the preferred embodiment of the medication detection subsystem 116 a plurality of the medication containers 402 may be installed within their corresponding container openings 406 in the portable medication holder 404 when the user being monitored is not removing medication from them. The medication containers 402 and the container openings 406 within the medication holder 404 maybe color coded. In this method the colors of a selected medication container 402 and its container opening 406 match each other. Likewise, each container opening 406 of the medication holder 404 may be provided with a matching colored light 408. The colored lights 408 assist the user in returning a removed medication container 402 to its correct container opening 406.

When a medication container 402 is disposed within a container opening 406 of the medication holder 404 the medication container 402 closes a conventional normally open switch 416. When the medication container 402 is removed from the opening 406 of the medication holder 404 it releases the normally open switch 416 causing it to open. When a switch 416 within the medication holder 404 is opened or closed in this manner by a medication container 402 a radio frequency medication transmitter 424 is activated. In this manner the medication self-management detection system 116 communicates this activity of daily living information with the system controller device 110.

The radio frequency signal provided by the medication transmitter 424 when it is activated by a switch 416 is pulse code modulated by pulse coder 420. The modulating of the pulse coder 420 is performed in a series of differing manners according to which switch 416 within the medication container 404 is opened. The selected pulse coded signal from the medication transmitter 424 is received, decoded, and stored by the system controller device 110 of the user monitoring system 100.

While the medication container 402 is removed from the medication holder 404 its matching colored light 408 is activated. This causes the color code of the medication container 402 removed from the medication holder 404 to be displayed as previously described. When the medication container 402 is replaced in its opening 406 of the medication holder 404 and the transmitter 424 is activated to transmit a corresponding pulse code modulated signal, the colored light 408 turns off and the transmission from the medication transmitter 424 to the system controller device 110 terminates. The termination of the transmission by the medication transmitter 424 indicates to the system controller device 110 that the medication container 402 has been returned to its opening 406 in the medication holder 404.

It will be understood by those skilled in the art that any number of medication openings 406 may be provided within a container holder 404 of the medication self-management detection subsystem 116. However, it is believed from current research that the daily medication management needs of a majority of users of the user monitoring system 100 may be met by eight medication openings 406 and eight corresponding medication containers 402 although only three are shown in order to simplify the drawings. It will also be understood that the openings 406 of the container holder 404 and the medication containers 402 may be provided with keying features so that only the correct medication container 402 may be placed into an opening 406 of the medication holder 404.

While the above describes many of the features of a preferred embodiment of the medication self-management detection system 116, it should be noted that various arrangements of medication holders and dispensers may be used. For example, the medications within a medication holder 404 may be organized according to the time of day they are taken. In this type of organization medications which are taken at the same time may be loaded together into a single compartment within the medication holder 404. A plurality of these compartments may be provided within the medication self-management detection system 116. The opening and closing of these compartments may be monitored by the medication self-management detection system 116 in substantially the same manner as previously described with respect to monitoring the removal of the medication containers 402 from the openings of the medication holder 404.

As previously described the pulsed transmissions from the medication transmitter 424 to the system controller device 110 may carry a plurality of differing codes corresponding to the plurality of differing medication containers 402. Each pulse code corresponds to an individual medication container 402 and indicates when its corresponding medication container 402 is currently removed from the medication holder 404.

The system controller device 110 of the user monitoring system 100 is programmed to record the times of removal and replacement of each medication container 402 within medicine holder 404 according to these transmissions. It is also programmed to determine scheduled on-time removals of each of the medication containers 404 from the medicine holder 404. Compliance data representative of these determinations according to transmissions from the medication self-management detection system 116 may be transferred to the case monitoring site 148 for intervention decisions.

The system controller device 110 of the user monitoring system 100 may be programmed to determine when user compliance does not conform to a scheduled regimen. After a selected time period, for example, one-half hour, without user compliance, voice data from the voice data storage device 224 may be applied by the controller device 110 to the in-home telephone 132 to remind the user to take medications. The system controller device 110 may also provide general and specific reminders and inquiries to the user concerning medications after the user returns from being away. These reminders and inquiries may be made with respect to all medications or with respect to specific medications. The system controller device 110 may also provide specific time scheduled reminders to take medication.

Figure 6:
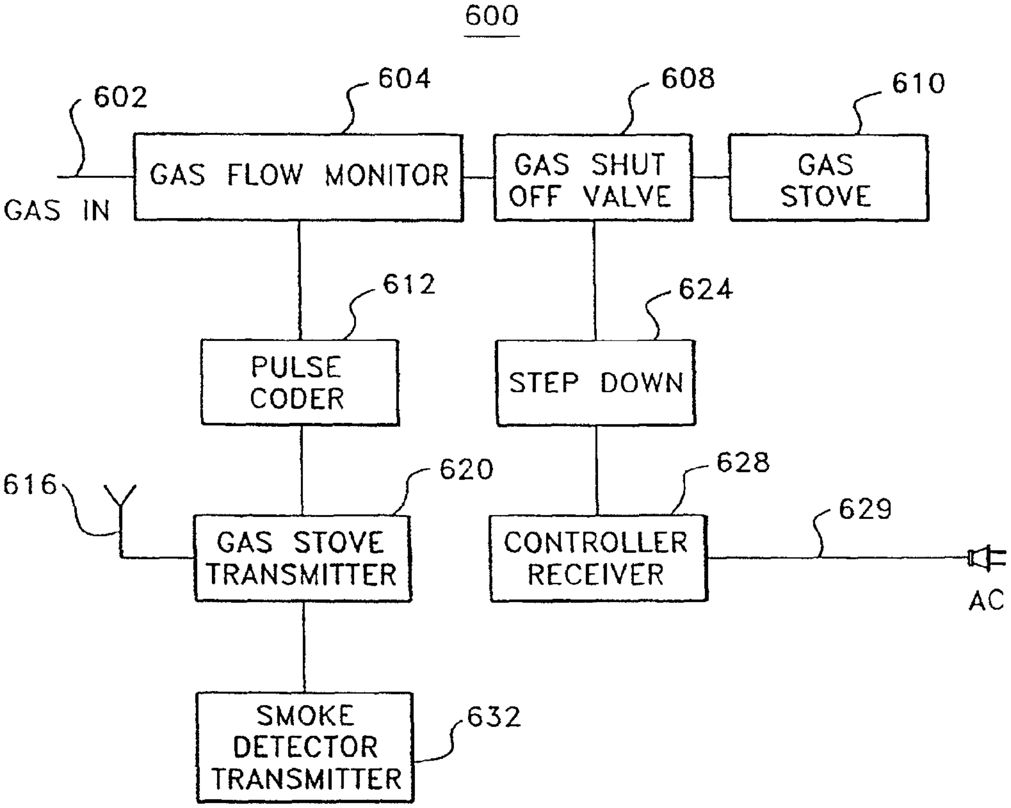
FIG. 6 is a block diagram representation of the gas stove safety detection subsystem of the user monitoring system of FIG. 1.
Figure 7:
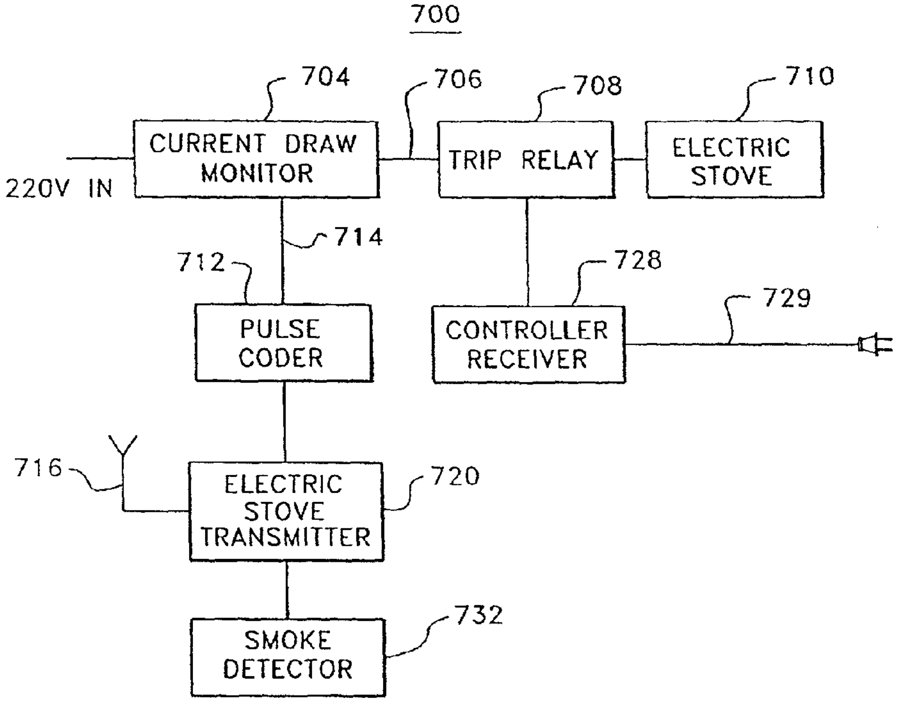
FIG. 7 is a block diagram representation of the electric stove safety detection subsystem of the user monitoring system of FIG. 1.

Referring to FIGS. 6, 7, there are shown two embodiments of the stove safety detection subsystem 120, the stove safety detection subsystem 600 and an electric stove safety detection subsystem 700. The stove safety detection systems 600, 700 of FIGS. 6, 7 are preferred alternate embodiments which are adapted for monitoring and controlling gas stoves and electric stoves, respectively.

The stove safety detection subsystems 600, 700 of the user monitoring system 100 each include an appropriate stove-in-use sensor for determining when a monitored stove is turned on. Each stove safety detection subsystem 600, 700 also includes an appropriate shut-off receiver unit for receiving a radio frequency transmission from the system controller device 110 by way of the AC lines to turn the monitored stove off and protect the user. The stove-in-use sensors of the stove safety detection subsystems 600, 700 continuously provide information to the system controller device 110 of the user monitoring system 100 regarding whether the monitored stove is currently on.

The stove-in-use sensor 604 of the gas stove safety detection subsystem 600 is a gas flow monitor 604. The gas flow monitor 604 is disposed in the gas line 602 which supplies gas to the gas stove 610 in order to monitor the gas supplied by the gas line 602 to the gas stove 610. Gas flow information from the gas flow monitor 604 is pulse coded by a pulse coder 612. The coded signal from the pulse coder 612 is transmitted to the system controller device 110 by a gas stove transmitter 620 by way of the gas stove antenna 616.

The system controller device 110 may determine that the gas stove 610 must be shut off in accordance with the coded information from the gas flow monitor 604. If this determination is made by the system controller device, it applies a control signal to the gas stove safety detection subsystem 600 by way of the AC line 630. The control signal to the gas stove detection system 600 from the system controller device 110 is generated and transmitted by way of the AC power line transmitter 216 as previously described. This control signal is received by the controller receiver 628 of the gas stove safety detection subsystem 600. The controller receiver 628 instructs a gas shut off valve 608 by way of a step down circuit 608 to terminate gas flow through gas line 602 to the gas stove 610 in response to the control signal. This turns off the gas stove 610.

When the user monitoring system 100 monitors an electric stove 710, an electrical current draw monitoring device 704 is provided for use along with the electric stove safety detection system 700. The electrical current monitoring device 704 is applied to the AC power line 706 which supplies power to the electrical stove 710. By monitoring the AC power line 706 detector subsystem 700 is able to indicate the on/off status of the burners of the electric stove 710. On/off status information is coded by the pulse coder 712 and transmitted by an electric stove transmitter 720 by way of antenna 716 to the system controller device 110.

The system controller device 110 may determine that the electric stove 710 must be shut off in accordance with the coded information from the current draw monitor 704 as previously described with respect to the gas stove safety detection system 600. If electric stove 710 is to be shut off, the system controller device 110 applies a control signal to the electric stove safety detection subsystem 700 by way of the AC line 730. This signal is received by a controller receiver 728 of the electric stove safety detection subsystem 700. The controller receiver 728 instructs the electrical trip relay 708 to interrupt electricity through the electrical power supply line 702 to electrical stove 710. This turns electric stove 710 off.

When the stove safety detection subsystems 600, 700 provide information indicating that a stove is on, shut down predetermined control algorithms are followed in order to determine whether the stove 610, 710 should be turned off.

These predetermined control algorithms are executed within the system controller device 110 of the user monitoring system 100. In the preferred embodiment of the user monitoring system 100 the algorithms operate upon coded information transmitted from the stove safety detection management subsystems 600, 700 and the movement detection subsystem 112 in the following manner although the other algorithms may be used if desired:

If (no movement detected for 30 minutes) or (away-mode status) and stove-on status), then (call with stove reminder).

If (no answer to call), then initiate shut down and record event. If (call is answered and 1 is pressed), override shut down.

If (stove on status) and (smoke detector tripped), then initiate shut down and record event.

If (stove is on for [X] minutes), then alert remote site host with automated telephone message: "Your stove is on, do you want it on? If yes, press 1; otherwise, it will be turned off." Answering the telephone and pressing 1 override the shutdown sequence.

Additionally, management subsystems 600, 700 may include smoke detector sensor devices 632, 732 coupled to radio frequency transmitters 620, 720. The smoke detection sensor devices 632, 732 may be standard optical smoke detector modified to include a subsystem switching circuit (not shown) which is effective to provide a smoke detect control signal when smoke is detected by the sensor devices 632, 732. The radio frequency transmitters 620, 720 of the smoke detection subsystem is coupled to the system switching circuit of the smoke detection sensor devices 632, 732 in a manner well understood by those skilled in the art.

When the sensor devices 632, 732 detect smoke within the home of the user they sound a fire alarm in a conventional manner. Additionally, the detection of smoke by the sensor devices 632, 732 activates subsystem switching circuit which activates the respective smoke detector transmitter 620, 720. In response the smoke detection transmitters 620, 720 provide a pulsed radio frequency control signal by way of the antenna 616. This control signal conveys information to the system controller device 110 of the user monitoring system 100. The information transmitted by the subsystems 600, 700 in this manner indicates to the system controller device 110 that smoke was detected by a sensor device 632, 732. It may also indicate which particular sensor device is triggered if more than one sensor device 632, 732 is used within a subsystem 600, 700.

Figure 8:
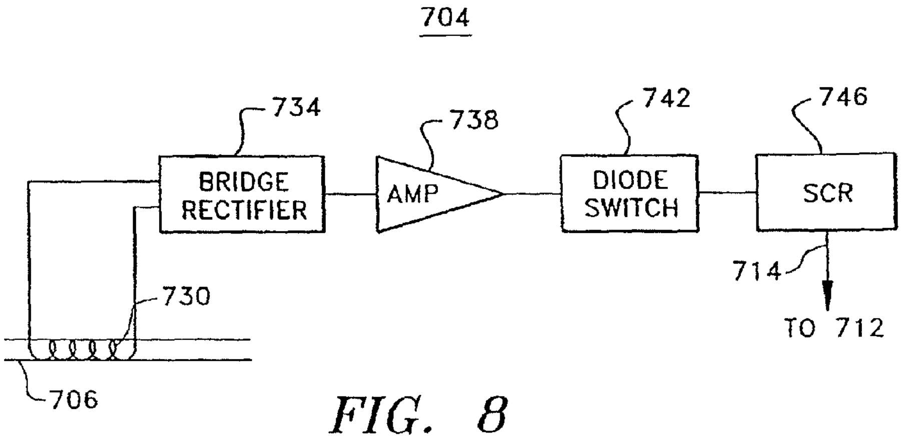
FIG. 8 is a more detailed schematic representation of the current drain monitor of the electric stove safety detection subsystem of FIG. 7.

Referring to FIG. 8, there is shown a more detailed schematic representation of the current draw monitor 704 of the electric stove detection subsystem 700. The current drain monitor 704 may include a passive clamp coil 730 disposed around the electrical supply line 706 which applies electrical energy to the electric stove 710. Electromagnetic fields arising from the current applied to the stove 710 by way of the electrical supply line 706 thus induce current in the passive clamp coil 730. The current induced in the passive clamp coil 730 may be rectified by a bridge rectifier 734, amplified by an amplifier 738, and applied to a diode switch 742. The diode switch 742 may then control the gate of silicon control regulator 746 to apply energy to the pulse coder 712.

It will be understood that any method may be used for sensing the electromagnetic fields arising from the current applied to the stove by way of the electrical supply line which induces current in the passive clamp coil 730, provided the current induced in the passive clamp coil is used to toggle an electronic switch of suitable design to control a pulsed radio frequency signal indicating to the system controller the on/off state of the stove 710. Additionally, it will be understood by those skilled in the art that pulse code 710 may be controlled by any other means for determining the state of stove 710.

Figure 9:
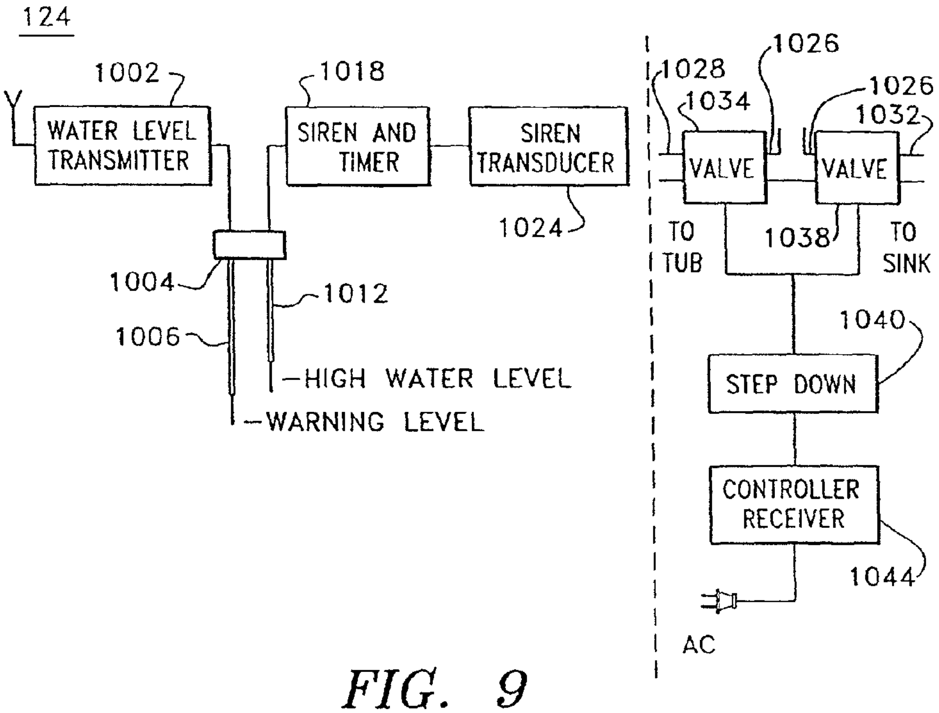
FIG. 9 is a schematic representation of the water overflow detection subsystem of the user monitoring system of FIG. 1.

Referring to FIG. 9, there is shown a preferred embodiment of the water overflow detection subsystem 124 of the user monitoring system 100. The water overflow detection subsystem 124 may be installed on plumbing fixtures such as sinks and bathtubs within the home of the user being monitored by the user monitoring system 100. Within the water overflow detection subsystem 124 a water level sensing device 1004 and a remote controlled shut-off device 1030 are provided in communication with the system controller device 110 of the user monitoring system 100.

In the principles of its operation, the water overflow detection subsystem 124 is similar to the gas stove safety subsystem 600 previously described. The water level sensing device 1004 or water level monitor 1004 sends information to the system controller device 110 by means of a pulsed radio frequency water level transmitter 1002. The system controller device 110 is programmed to initiate shut off of water within overflow detection subsystem 124 by means of a radio frequency remote control signal. The radio frequency remote control signal is transmitted through the home of the user by way of the AC lines.

The control signal from the system controller device 110 is received by the controller receiver 1044, stepped down by step down circuit 1040. The stepped down signal is used to control resetable electrically controlled water valves 1034, 1038. The electrically controlled valve 1034 may control water flow from an inlet pipe 1026 to a tub supply pipe 1028. The electronically controlled valve 1038 may control water flow from an inlet pipe 1026 to a sink inlet pipe 1032.

The water level sensing device 1004 includes two water level detectors 1006, 1012, and a siren module 1018 having a conventional timer. A siren transducer such as a piezoelectric crystal is also provided. A three-state pulsed radio frequency transmitter 1002 may be provided within the water overflow detection subsystem 124.

When water is sensed at a warning level by the level detector 1006 the system controller device 110 of the user monitoring system 100 is informed that water is approaching the warning level mark. When this is detected the user monitoring system 100 calls the user on the in-home telephone 132 in order to provide a reminder. When the level detector 1012 determines that the water level has approached the high water mark, the siren 1024 sounds. Additionally, the received radio frequency pulse data informs the system controller device 110 of the user monitoring system 100 to turn the water off. This event is logged within the system controller device 110. The water overflow detection subsystem 124 may be programmed to permit resetting of the valves 1034, 1038 in response to commands from within user monitoring system 100 or from the case monitoring site 148.

Figure 10:
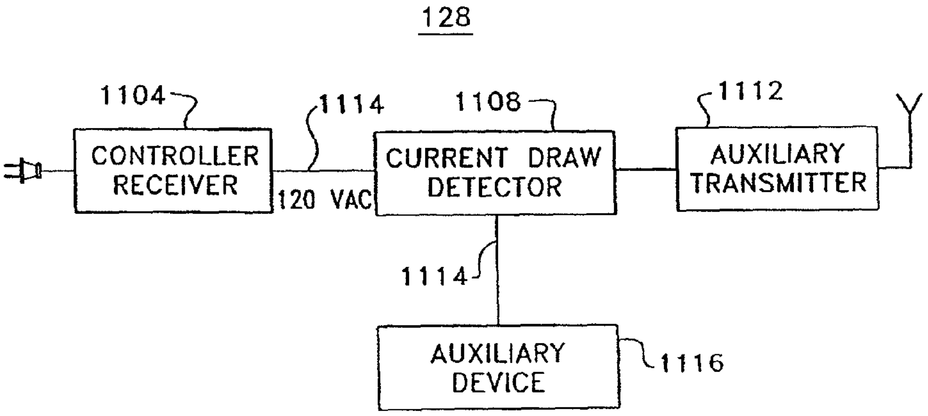
FIG. 10 is a block diagram representation of the auxiliary appliance detection subsystem of the user monitoring system of FIG. 1.

Referring to FIG. 10, there is shown a block diagram representation of the auxiliary appliance detection subsystem 128 of the user monitoring system 100. The auxiliary appliance detection subsystem 128 provides additional channels to the user monitoring system 100 for monitoring and controlling further appliances 1116 or devices 1116.

The on/off state of the further device 1116 is monitored and transmitted to the system controller device 110 of the user monitoring system 100 by means of a current draw detector 1108. The current draw detector 1108 monitors current applied to the device 1116 by way of the AC power supply line 1114. The current draw detector 1108 is coupled to a radio frequency auxiliary transmitter 1112 which transmits a two state signal representing on and off. This information may be used by the system controller device 110 both for status change data and for generating a daily activity data log. The current draw sensor 1108 of the auxiliary detection subsystem 128 should be sufficiently sensitive to distinguish between trickle draw and operational power when auxiliary device 1116 is a solid state device such as a television or a clock radio.

In addition to the monitoring of the use of a auxiliary device 1116, automatic remote control of the device 1116 may be accomplished. The system controller device 110 of the user monitoring system 100 may be programmed to control a controlled outlet or receptacle adapter which applies energy to the AC line 1114. This control may be exercised at predetermined times of the day or upon certain environmental occurrences. For example, when the user monitoring system 100 is in the away mode this feature may be used to automatically turn the auxiliary appliance 1116 off. More than one auxiliary subsystem 128 may be provided within the user monitoring system 100.

Furthermore, monitoring system 100 may be provided with an auxiliary detection system which is not monitored by a current draw monitor 1108 or controller receiver 1104. For example, the multichannel receiver 212 of system controller 110 may be used to monitor smoke detection subsystem 900 shown in FIG. 9.

It will be understood that many differing combinations of auxiliary detection subsystems may be provided within the user monitoring system 100 of the present invention. It will also be understood that these combinations may be used in combination with automated dialing systems at other locations. Automated dialing systems which may call the dwellings of various users, for example, one or more times a day have been developed. This provides the user with an opportunity to return a predetermined signal if there are no problems and return a different predetermined signal or no signal if there are problems.

These services may give users up to six automated contacts per day. For example, an automated dialing system for providing medication compliance reminders, suitable for use with the user monitoring system 100, has been field tested. In this automated reminder system users were called daily and reminded to follow their medication regimen.

Figure 11A:
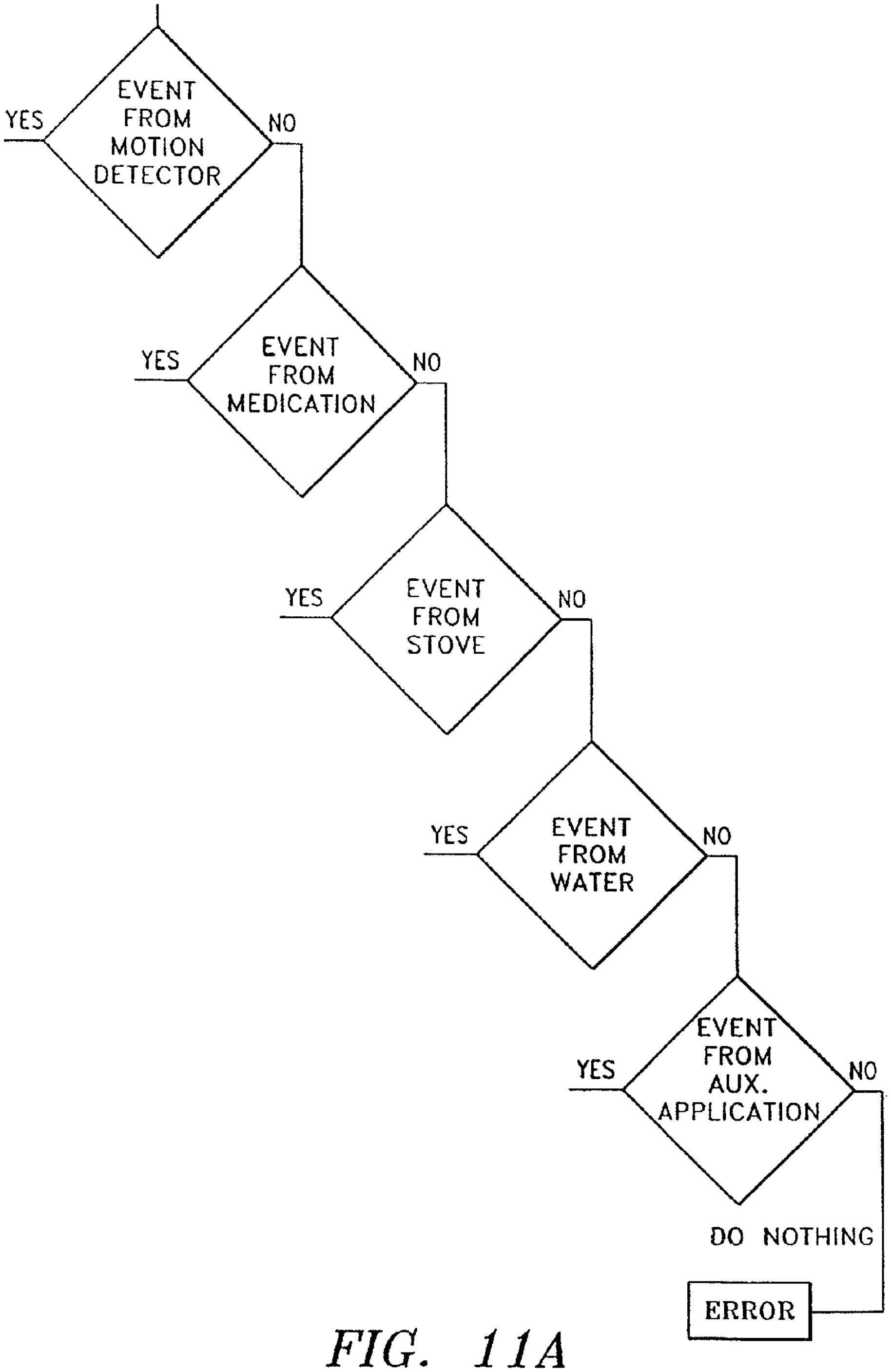
FIGS. 11A-11M are flow charts representing operations performed with respect to the various subsystems of the system of FIG. 1.
Figure 11B:
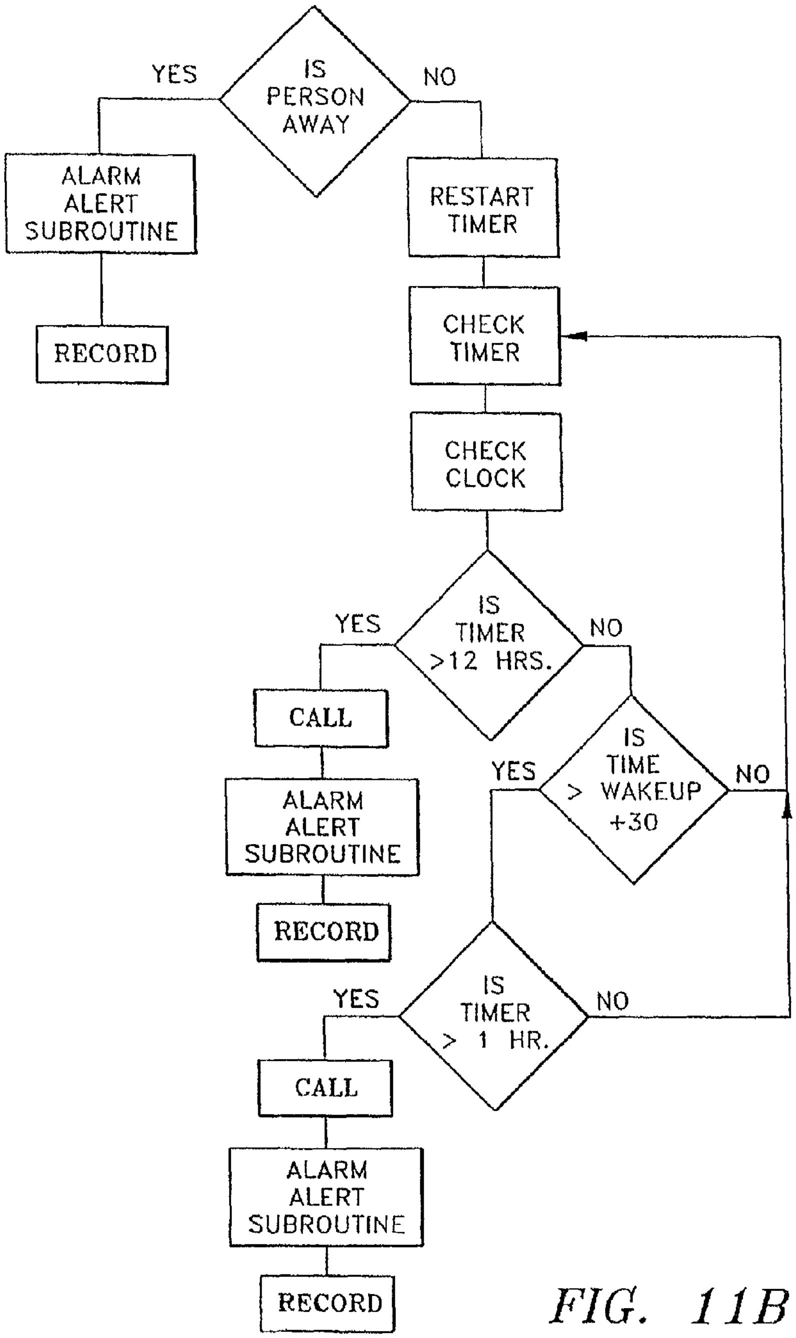
Figure 11C:
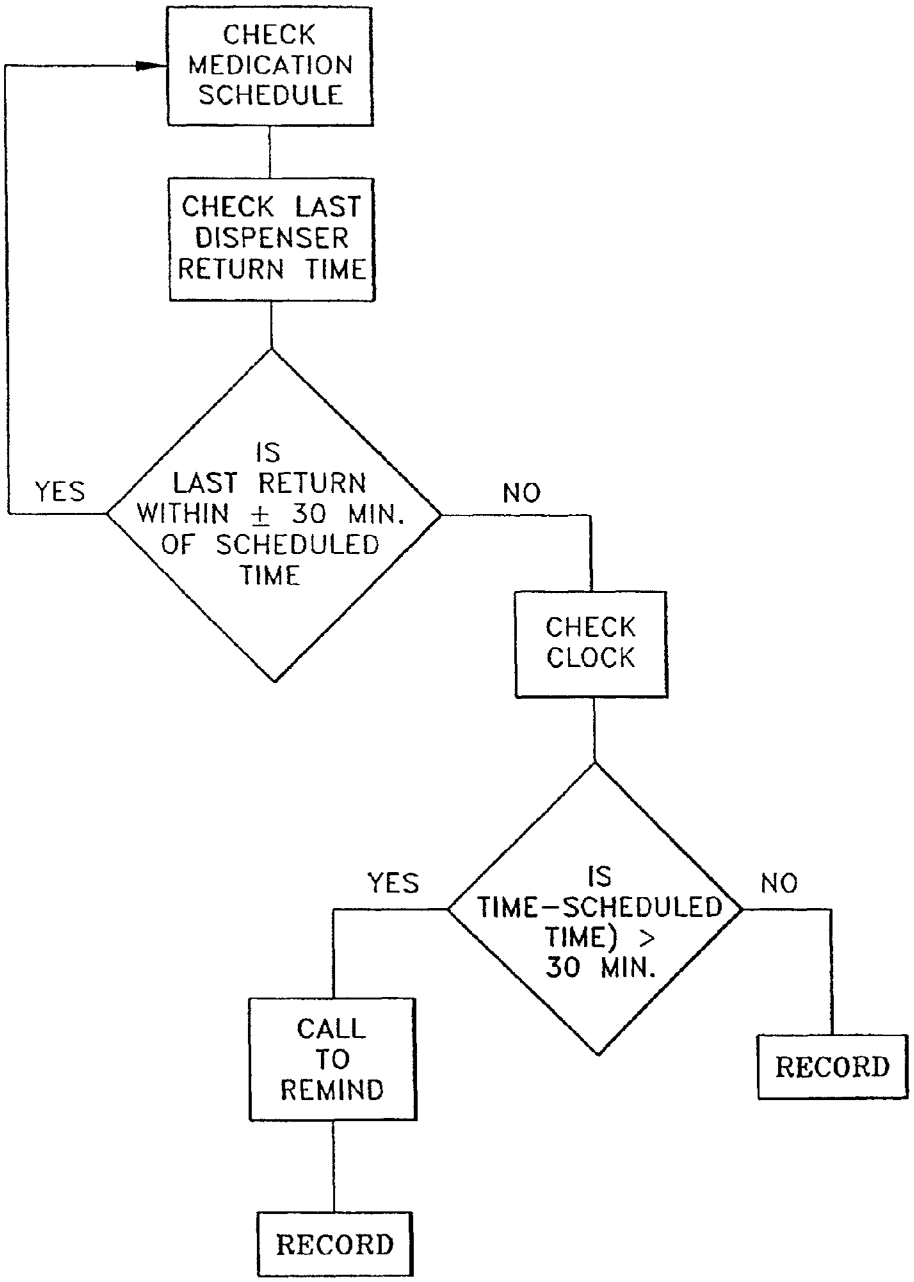

Referring to FIGS. 11A-11M, there are shown flow chart representations of the operations of the various subsystems of the user monitor system 100. FIG. 11A is a flow chart representation of a method for determining which of the various subsystems has initiated an event for processing by the controller 110. FIG. 11B is a flow chart representation of a method for determining whether the user has arisen by a designated wake up time. This method may be performed in response, for example, to a signal from the motion sensor 304. FIG. 11C is a representation of a method for determining whether the user is complying with the medication schedule as indicated by the subsystem 116.

Figure 11D:
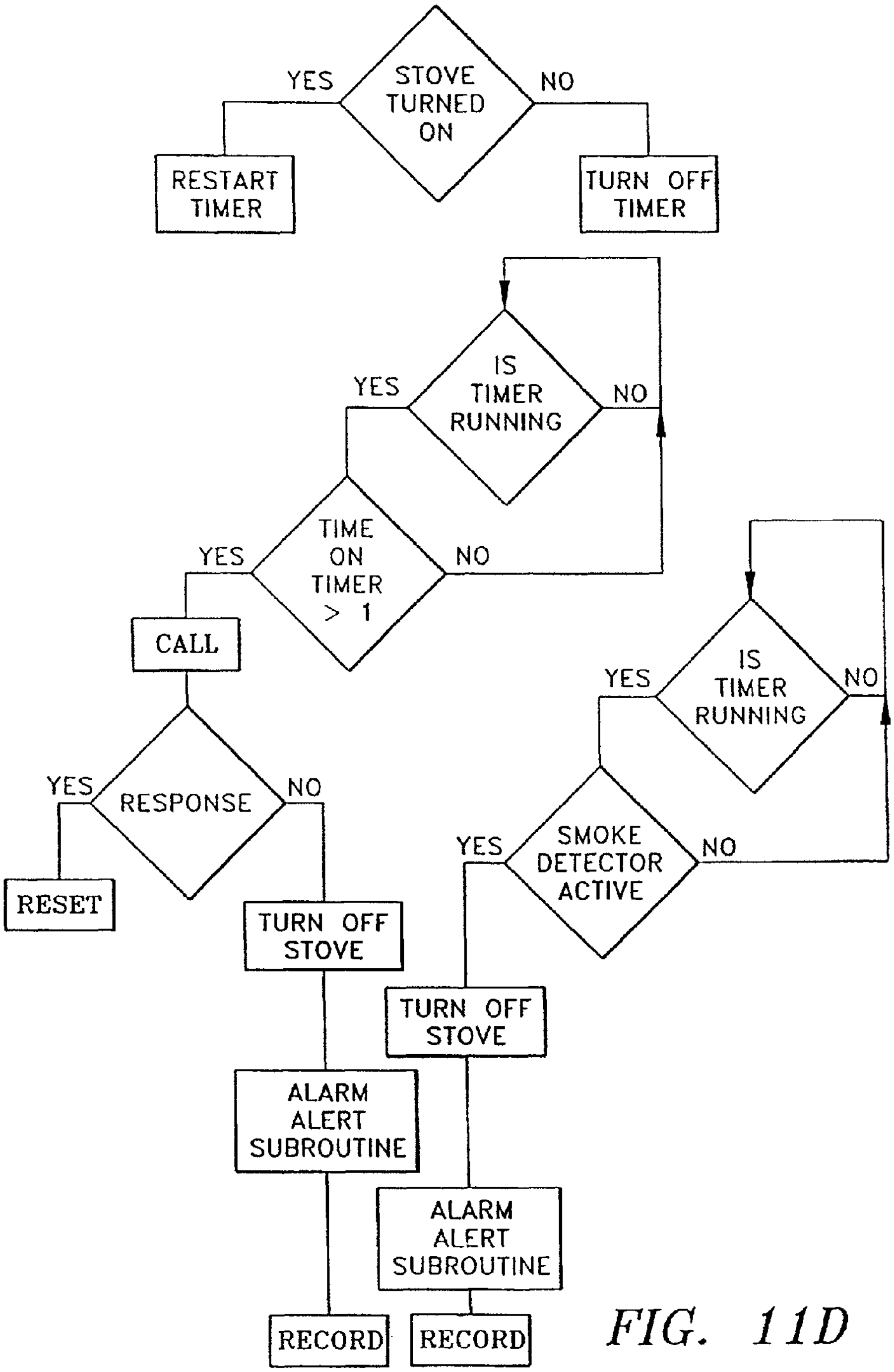
Figure 11E:
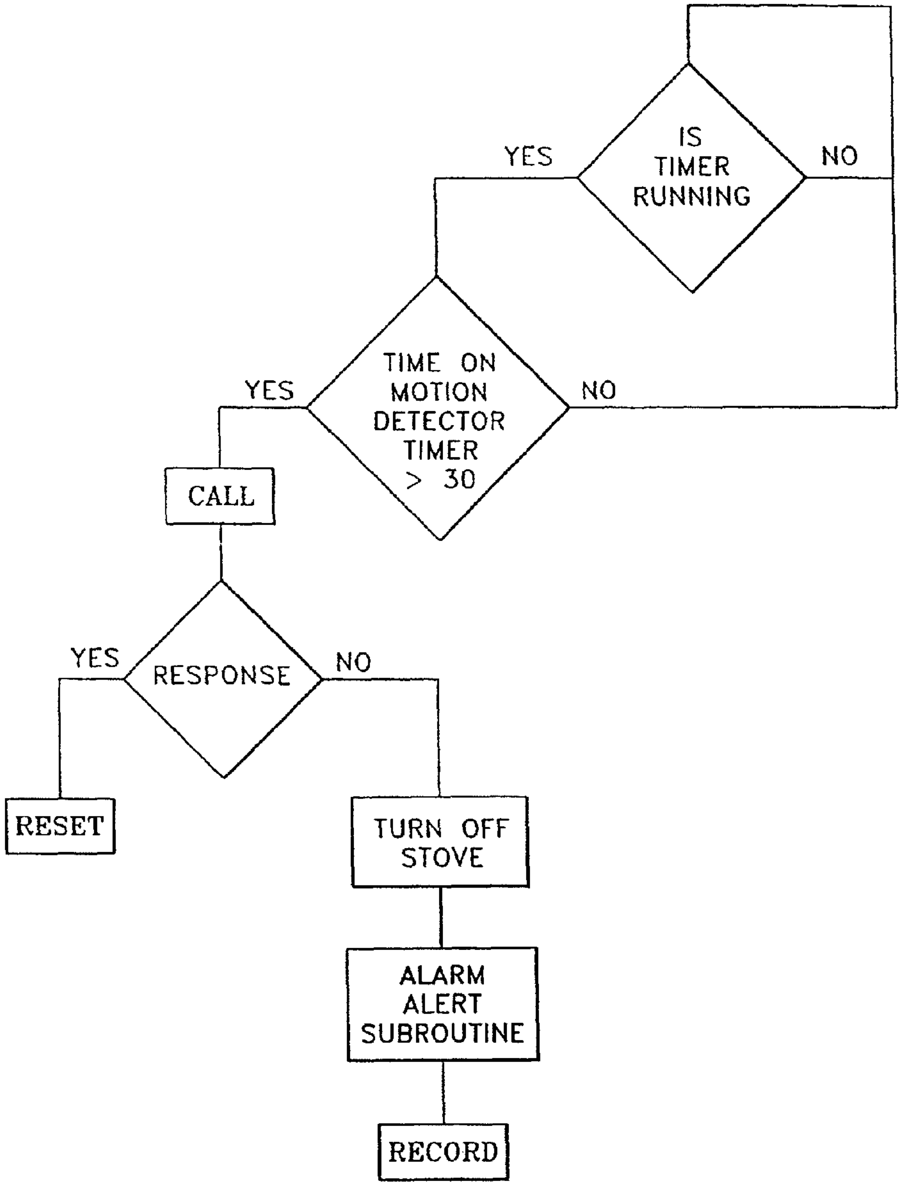
Figure 11F:
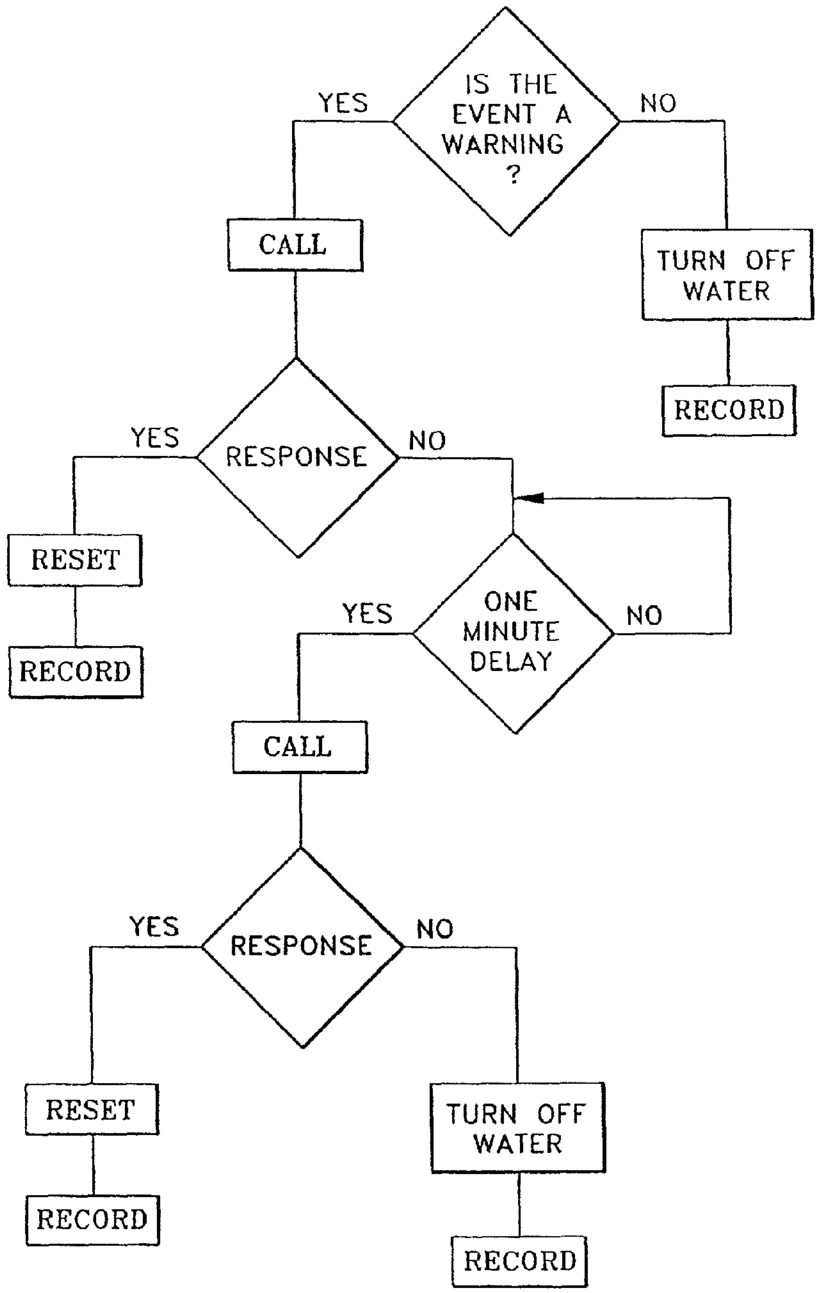

FIG. 11D is a representation of methods for determining whether a stove has been left on according to the subsystem 600 and whether the smoke detector 732 has been activated. FIG. 11E is a flow chart representation of a method for turning off the stove 610, 710. FIG. 11F is a flow chart representation of a method for controlling water flow according to the subsystem 124. A pseudocode representation of a method for controlling water flow is set forth in Table I.

1 TABLE I Is there a flow If yes Is there a change of state If yes send event to main controller If no recycle to flow monitor If no Is there a change of state If yes send event to main controller If no recycle to flow monitor Is there water overflow If yes Send event to main controller If no Is there water warning If yes send event to main controller If no recycle to water overflow.

Figure 11G:
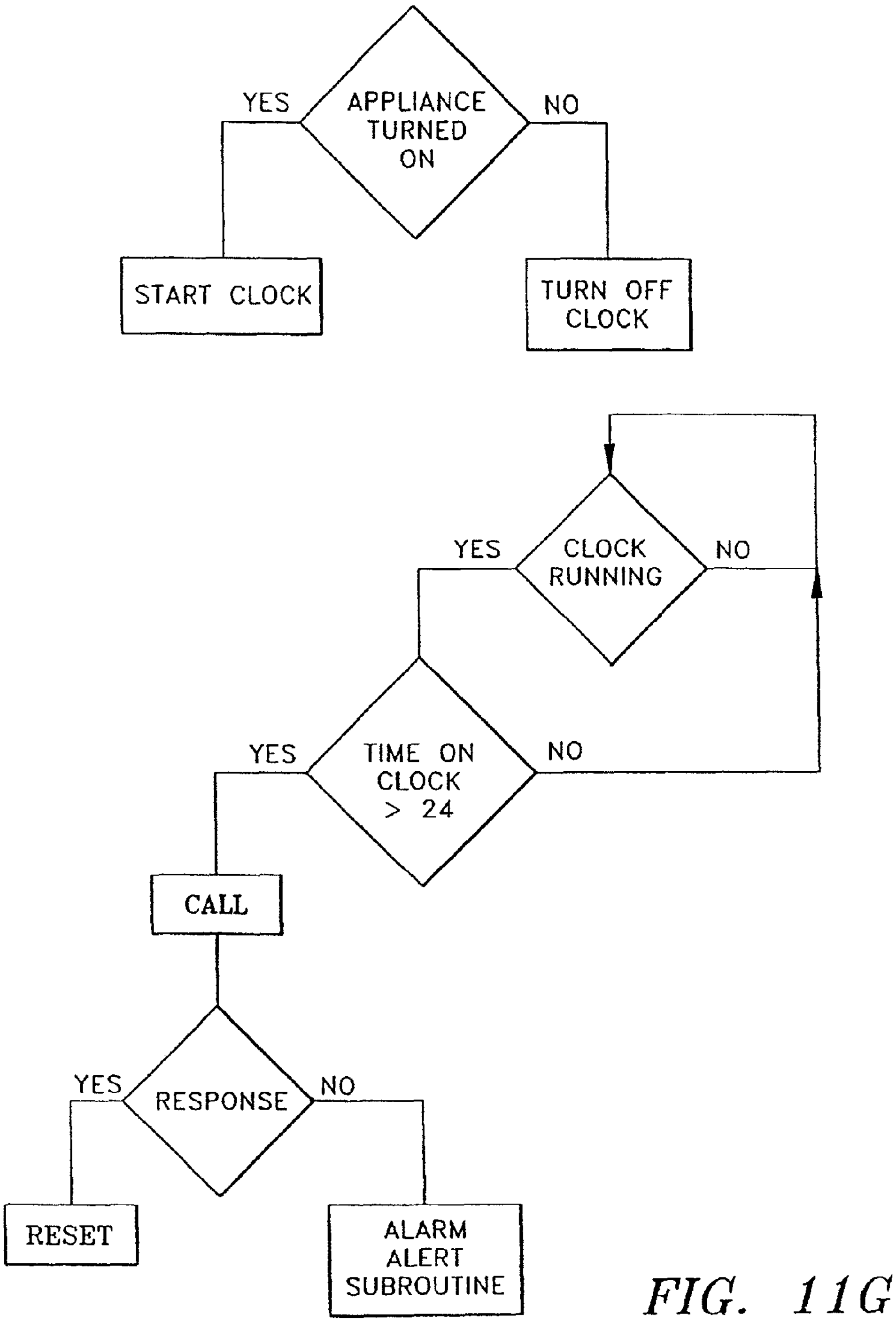

FIG. 11G is a flow chart representation of a method for alerting a user that an appliance has been left on, for example, in accordance with the bridge rectifier 734.

Figure 11H:
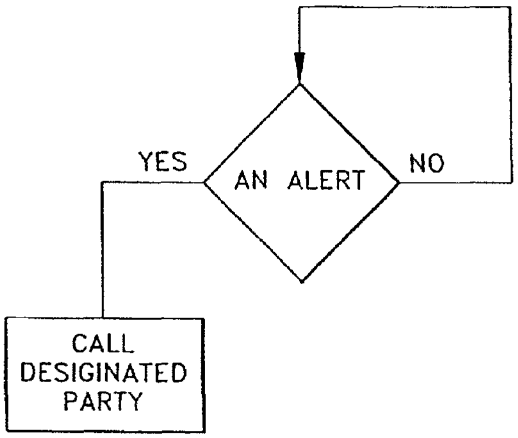
Figure 11I:
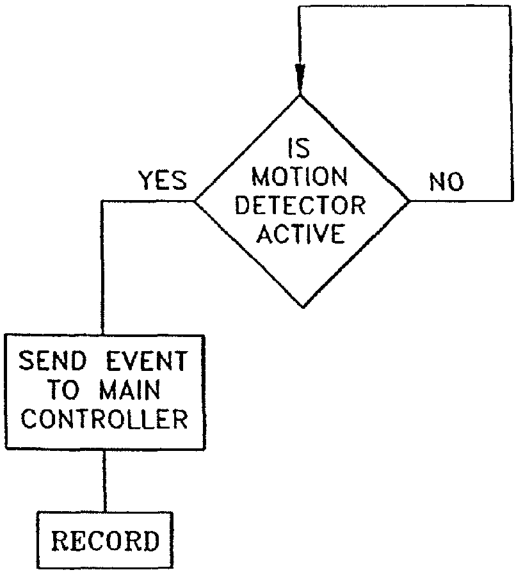

FIG. 11H shows a method for calling a designated party when an alert has been determined. FIG. 11I shows a method for recording the detection of movement, for example, in response to a signal from the motion sensor 304.

Figure 11J:
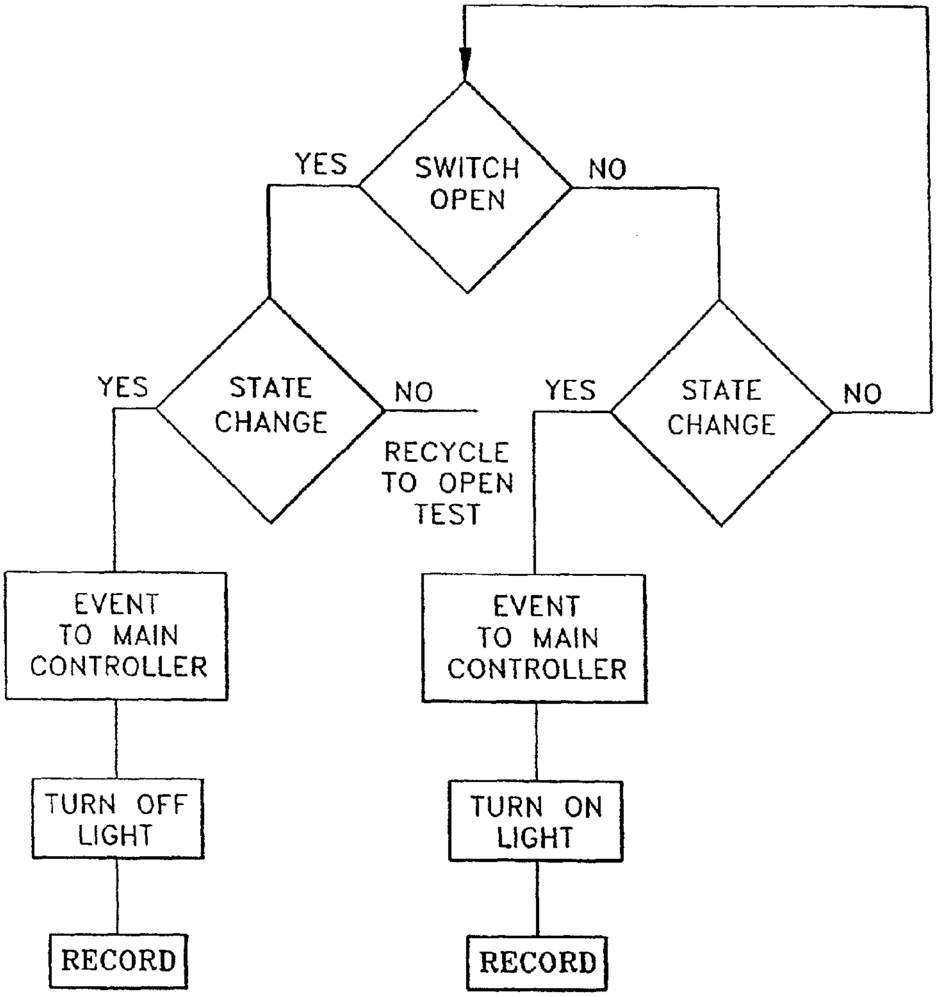

FIG. 11J is a flow chart representation of a method for reading switches within the user monitoring system 100. A pseudocode representation of a method for reading switches is set forth in Table II.

2 TABLE II Is the switch open If yes Is there a state change If yes send event to controller turn off light If no recycle to open test If no Is there a state change If yes send event to main controller turn on light If no recycle to open test.

Figure 11K:
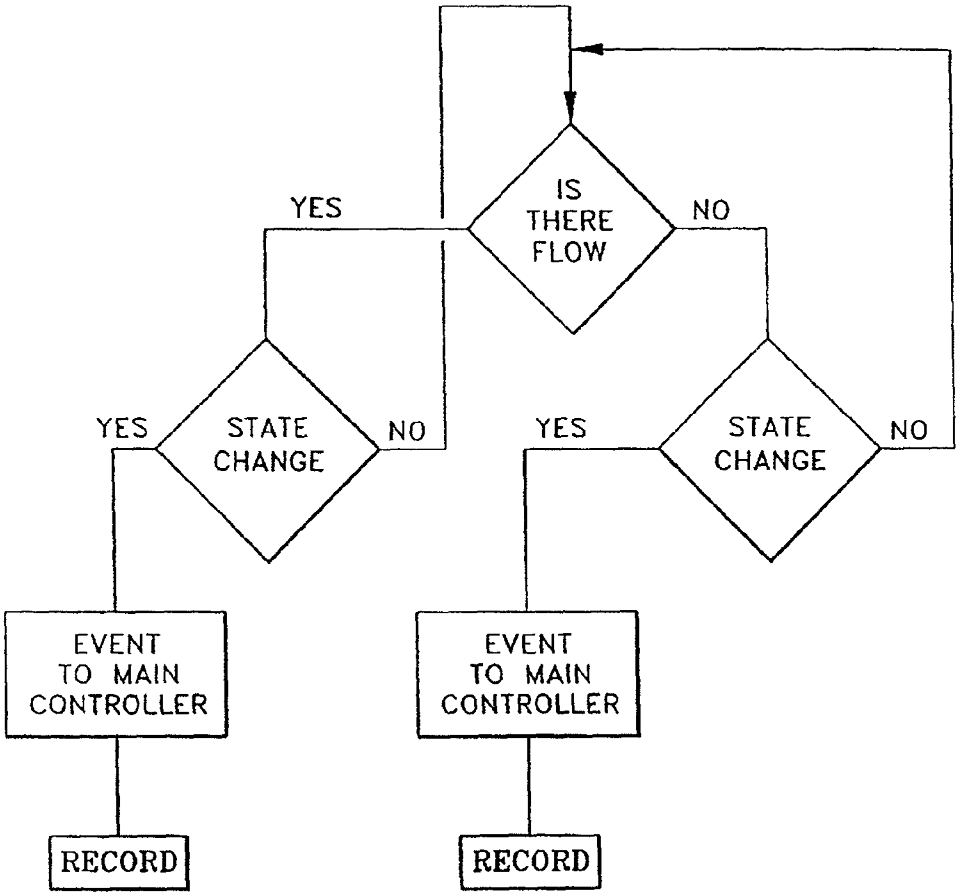
Figure 11L:
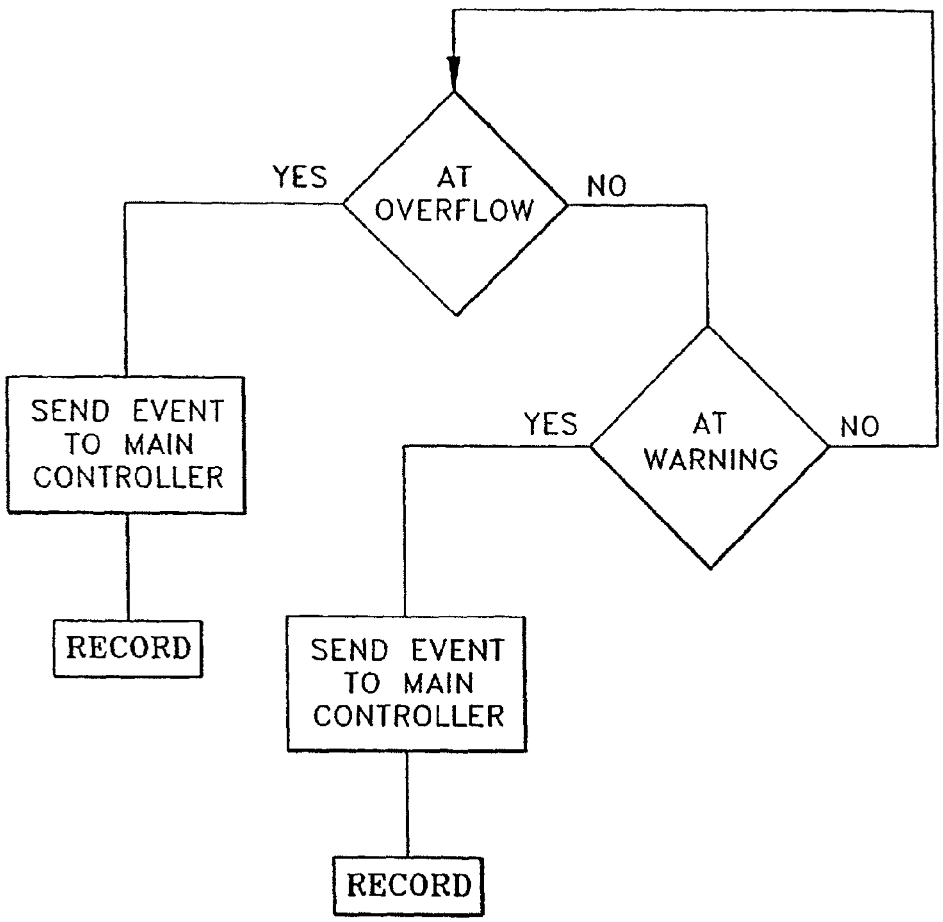
Figure 11M:
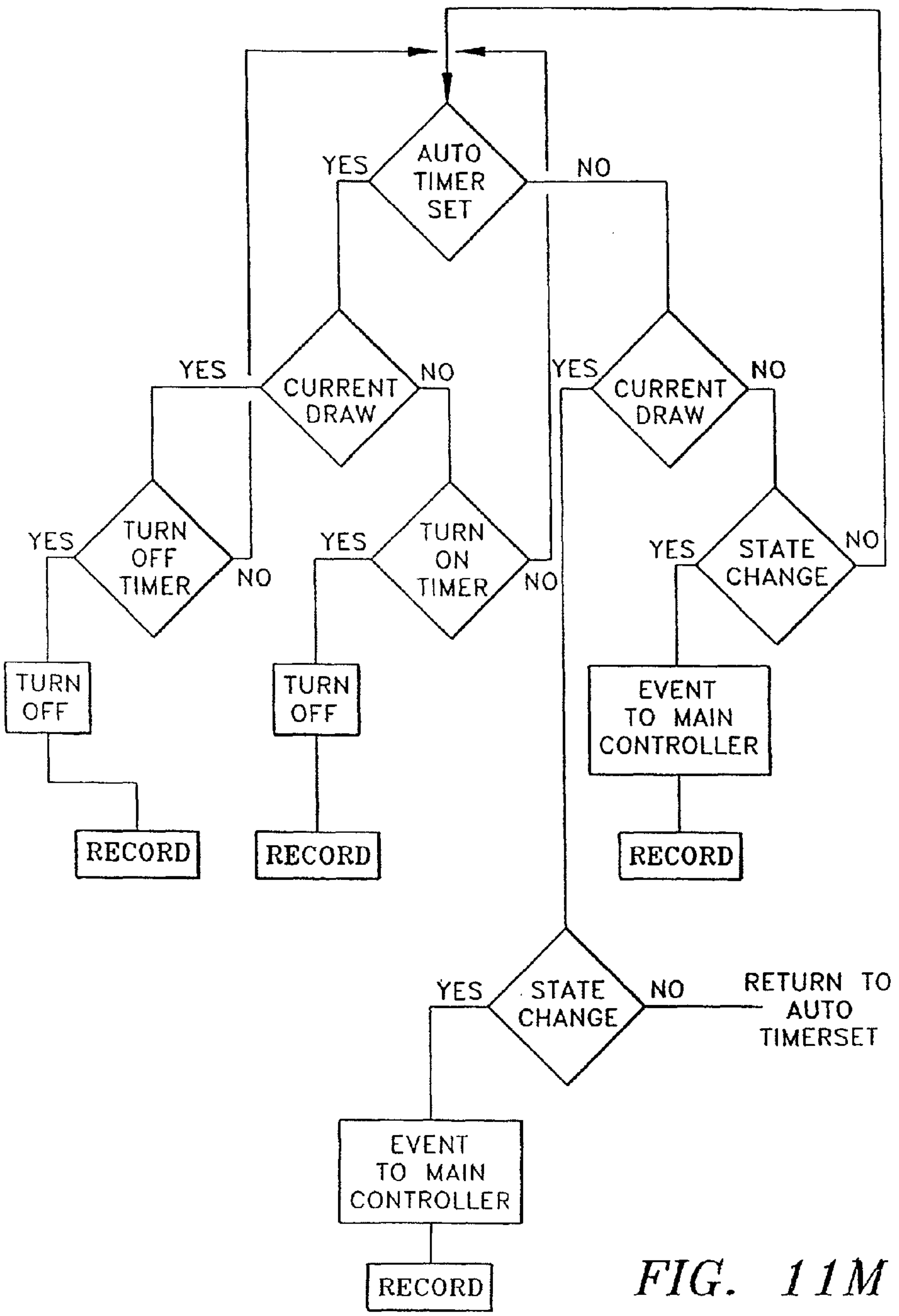

FIG. 11K is a flow chart representation of an algorithm for determining either current flow or gas flow. FIG. 11L is a flow chart representation of an algorithm for detecting water overflow. FIG. 11M is a flow chart representation of an algorithm for controlling an auxiliary appliance. A pseudocode representation of this method is set forth in Table III.

3 TABLE III Is the automatic timer set If yes Is there current draw If yes Is turn off timer exceeded If yes turn off appliance send event to controller If no recycle to AT set If no Is turn on time exceeded If yes turn on appliance send event to controller If no recycle to AT set If no Is there current draw If yes Is there a state change If yes send event to main controller If no recycle to AT set If no Is there a state change If yes send event to main controller If no recycle to AT set.

As previously described, using the microprocessor based system controller device 110 and a system of sensors the user monitoring system 100 can determine, for example, whether users are up and about in their homes and whether they are having difficulty managing their medications. It can also be determined whether the user has accidentally left a stove on or has failed to get out of bed a predetermined number of hours after a usual waking time. If the user monitoring system 100 detects any of these or other problems it can then call the user on the in-home telephone 132 to provide a reminder about the medications, stove, or other detected problems.

Using this data from the user monitoring system 100, the remote case monitoring system 148 may provide on-line case monitoring of each user by receiving standard information and information designated as priority information and analyzing the received information. In order to do this, the remote case monitoring system 148 converts incoming data on each user into various summary reports which track the activities of the client. This makes it possible to distribute specialized gerontological every day living summary reports to users, family members, case managers, physicians and others. It also makes it possible to collect and act upon the designated priority information which may indicate immediate problems for the user. For example when a user appears not to have gotten out of bed a problem may be indicated.

Additionally, the collection of this kind of data by the remote case monitoring system 148 may provide an aggregate data base for identifying which users require personal interventions and which do not. In order to perform these functions the remote case monitoring system 148 serves as a central hub for the collection, analysis and exchange of information which has direct case management import. It should be understood that in different embodiments of the inventive concept different degrees of autonomy of the local system controller 110 in relation to the remote system 148 are possible. In one embodiment a local system controller 110 may be programmed to perform many functions performed by the remote case monitoring system 148 in another embodiment.

For example the dialing and sending of voice messages to a list of relatives and providers may be performed either by the local system controller 110 or the remote case monitoring system 148. However, it will be understood that the primary function of the local system controller 110 is to provide lower level case management of local observations and decisions and the primary function of the remote case monitoring system 148 is to provide higher level case management to enable long term interpretation of the data obtained from the user monitor system 100 and intervention in view of the long-term interpretation.

Thus in the preferred embodiment of the present invention, the user monitoring system 100 or the remote case management system 148 may use its electronic records to enable the production of scheduled periodic user activity reports based upon information gathered by the various subsystems of the user monitoring system 100. These periodic reports may include collections, compilations and arrangements of information on any or all of the monitored activities within the user's living area. These electronic records may be used in combination with any other information to produce any type of periodic activity reports desired on the user being monitored. These user activity reports may be used by a professional case manager or a designated family member to determine if the user is experiencing problems with specific activities of daily living. Thus these problems may be dealt with before they become a threat to the continued well being of the user and the ability of the user to live independently.

Furthermore, in addition to providing remote case monitoring and in-home reminders, the user monitoring system 100 may be programmed to take corrective actions when certain problems are detected. For example, if the user being monitored has not gotten out of bed by a predetermined time the user monitoring system 100 may call the user on the telephone 132. If there is no answer to the telephone call the user monitoring system 100 may be programmed to automatically transmit this information to the remote case monitoring site 148.

A social worker, health professional or designated family member at the remote case monitoring site 148 may respond to the transmitted information according to a predetermined protocol. In addition to transmitting the information to the remote case monitoring site 148 the user monitoring system 100 may provide control signals within the home of the user. For example, if the user monitoring system 100 of the present invention determines that a stove has been left on, the user monitoring system 100 itself can turn off the stove.

The remote case monitoring system 148, in association with the user monitoring system 100, may serve the functions of a case management site. In an example of the case management site function of the remote case monitoring system 148 the case management site may monitor approximately fifty distributed clients, each using a distributed user electronic monitoring system 100. The fifty clients thus have the system controller 110 and various subsystem sensors installed in their dwellings in ways appropriate for the specific configuration of their living areas. For example, the various subsystem sensors must be adapted for different floor plans and furniture arrangements.

The remote case monitoring system 148 may receive information from the distributed user monitoring systems 100 on an immediate basis or at predetermined time intervals. For example, the remote case monitoring system 148 may receive information hourly, daily or weekly basis. If one of the clients does not get out of bed within a predetermined time duration and does not answer the telephone, the local system controller 110 of the user monitoring system 100 at that client's house may call the case management site. At the case management site, this event may be brought to the immediate attention of the human case monitor, for example, by means of a computer screen. The remote case manager may examine individual: case and data records for the client being monitored to learn the predetermined response for the monitored person when the reported event occurs.

Likely interventions required of personnel at the case management site may include calling a local case manager, a hospital social worker or a local next of kin. Other actions the remote case monitor may execute include calling the user, remotely downloading the last twenty-four or forty-eight hours worth of event summary information from the local user monitoring system 100 and remotely initiating a diagnostic sequence on the local user monitoring system 100.

The protocol of procedures for intervention by the remote case monitor 148 may differ from one remote case monitoring system 148 to another and from one user to another. It is anticipated in the preferred embodiment of the invention that various intervention decisions such as who to call when predetermined events occur and what messages to deliver may be carried out by a machine intelligence expert system (not shown) at the remote case monitoring system 148 or by a person or a combination of both. The local user monitoring system 100 may also be programmed to carry out such decisions as who to call when appropriate. For example, the user monitoring system 100 may have a contact list of people to contact in various emergencies.

In addition to receiving and interpreting data indicating the need for intervention in event of emergencies, the remote case monitoring system 148 routinely receives downloaded data from individual user monitoring systems 100 at predetermined intervals. This data is interpreted on the individual and aggregate level by means of trend analysis software which detects larger than statistically normal deviations from event pattern measurements. The remote case monitoring system 148 may use this analysis to produce periodic summary reports of events relating to everyday living tasks in the home environment of the user. More specifically these reports may be used to detect certain event classes, to weight them in terms of their relative importance and to compare them with baselines of task performance. The events weighed with respect to their importance may include getting out of bed, managing medication, the proper control of a stove, the proper control of water flow, and the proper control of selected electrical appliances. Based upon the reports of these events, gerontological living summary reports may be prepared in machine form and paper form at the remote case management system 148 for distribution to predesignated parties involved in the case management of the user of the user monitoring system 100. These parties may include the users themselves, relatives of the user, case manager social workers, physicians and other appropriate formal and informal providers.

Two additional functions of the remote case monitoring system 148 may be provided. These functions are: (1) the remote programming and reprogramming of the user monitoring system 100, and (2) the generation of aggregate and individual level data on relatively large numbers of users. This data may serve both as an empirically grounded knowledge base driving the decision protocols for both humans and machines as well as research data for further development of the user monitoring system 100.

In order for these functions to be performed data must be transmitted between the user monitoring system 100 and the remote case monitoring system 148. Information transmitted to the system controller 110 of the local user monitoring system 100 from the remote case monitoring system 148 may include three different types of commands: queries, diagnostics and settings. The query commands request the downloading of specific information from the memory of the user monitoring system 100 to the remote case monitoring system 148. The requested information forms the basis of the gerontological everyday living events report along with specific information necessary for case monitoring by the remote system 148. For example the status of different subsystems of the user monitoring system 100 might be made available to the remote system 148 when the motion subsystem 112 indicates that the user has not gotten up in the morning.

The diagnostic commands to the local user monitoring system 100 test the different subsystems of the system 100 by suppressing the ability of the system 100 to either call out interventions or change settings on any of the remotely controlled devices while at the same time initiating a sequence of event codes which indicate the presence of various kinds of problems as if they were indicated by the different subsystems.

The setting commands from the remote case management system 148 to the user monitoring system 100 reset the parameters on the timers within the user monitoring system 100 as well as other variable values for the decisions made in the decision trees described herein below. These parameters may include, but are not limited to, the time of waking up, the times for taking different medications and the length of time which should elapse prior to turning off the stove.

Transfer information transmitted in the opposite direction, from the system controller 110 of the user monitor system 100 to the remote case monitoring system 148, includes two types: (1) priority specific data transfer and (2) standard data transfer. Priority specific data transfer is initiated by the local system controller 110 by means of dialing the remote case monitoring system 148 by way of the telephone line 144 or by means of another data link (not shown) and indicating the presence of a problem which the remote case monitoring system 148 must detect, record and act upon.

Situations in which the local system controller 110 dials out to inform the remote case monitoring system 148 that the user did not get out of bed or that the stove was left on, are potential emergencies and are therefore examples of priority specific data transfer. Standard data transfer includes the downloading of event log information for each subsystem. This information is used to produce trend analysis reports which show the frequency of occurrence of different events over a predetermined time period such as six months. Thus the trend analysis report might show that over the course of six months the user became increasingly noncompliant with medications and/or increasingly likely to leave the stove on inappropriately. Using a known trend analysis technique, software driven reports can detect increasing frequencies of problems of every day activities.

The trend analysis report may be a monthly paper or machine report which provides several indicators of performance on different areas of everyday living monitored by the user monitoring system 100. These areas may include waking and sleeping, medication management, stove management, water flow management and the operation of additional appliances. The raw data for this report is based on the event log data transferred from the local system controller 110 remote system using standard data transfer and priority specific modes. The raw data is used to provide a continuous baseline of the successful and not successful completion of the five task areas.

For example, in one month a user may use the stove fifty-five times and leave it on in violation of the programmed protocol two times. The monthly report line for the stove category might then show fifty-five uses and two usage errors. Furthermore, usage errors may be classified according to level of importance by means of a weighting system. An error of, for example, skipping one medication may be weighted as considerably less significant compared with an error of leaving the stove on and leaving the apartment for several hours. Thus not only are errors recorded and plotted against continuous baselines overtime in the trend analysis report of the system of the present invention, but the report is intended to contain a ranking system to reflect the potential negative impacts of different errors.

In addition to errors, the trend analysis report can plot deviations in behavior indicating changes in plot trend. For example, the trend analysis report can plot waking and sleeping hours and the number of times a user goes to the bathroom. While none of this in itself indicates a situation requiring intervention, sudden changes in sleep habits, bathroom use, even appliance use may indicate sudden changes in health or cognitive well being requiring a relative or a case management social worker or case management social worker or a physician to visit or interview the user.

While any number of combinations of interpreted data can be used in any number of specialized reports, it is anticipated that most case management sites and most relatives would want to know the frequency and severity of specific errors, the extent and accuracy of medication compliance and whether a waking or sleeping pattern of a user is changing radically. The trend analysis report provides case managers and relatives with this information and enables them to better help the user by locating subtle changes in behavior patterns, monitoring various kinds of potentially dangerous errors and keeping a record of baseline functioning in relation to monitored activities.

While the operation of the monitoring system 100 has been described principally with respect to the monitoring of a gerontological patient, it will be understood that system 100 may be used to monitor any type of patient, for example, infants and burn victims. Additionally, it will be understood that, using the correct sensors, monitoring system 100 may monitor any parameters relevant to these patients, for example, ambient temperature, body temperature and blood pressure. In general, anything which may be sensed by a sensor and converted into an electrical signal may be monitored by the monitoring system 100. Additionally, the data could be made available to a doctor prior to routine doctor's appointments in addition to being used to compile reports at the remote monitoring site 148. The system could be monitored by a friend or relative rather than by professionals at a remote monitoring site.

Local microprocessor based system controller 110 and its associated system of sensors can determine any activity of daily living desired. For example, system controller 110 can determine whether users are up and moving around in their homes. Additionally, it can determine, for example, whether the user is having difficulty managing medications, whether the user has failed to get out of bed a predetermined number of hours after a usual waking time, and whether the user has left the stove on. Furthermore, system controller 110 can determine other detected problems.

As previously described, various degrees of autonomy of local system controller 110 from remote monitoring system 148 can be obtained in various embodiments of the invention. Thus, system controller 110 can be programmed to perform many functions performed by remote monitoring system 148 in other embodiments of the invention. However, it is understood that the primary function of local system controller 110 is to provide lower level case management of local observations and decisions and the primary function of remote monitoring system 148 is to provide higher level case management and enable long term interpretation of the data.

Using the information sent from local system controller, remote case monitoring system 148 can provide on-line case monitoring of any number of users by receiving standard priority information or other information and analyzing the received information. When performing these operations remote case monitoring system 148 converts incoming data on each user into various summary reports which track the activities of the individual users.

Monitoring and analyzing the received information in this manner makes it possible for remote case monitoring system 148 to distribute specialized everyday living monitoring summaries (ELMS) reports to other parties. For example, the reports obtained in this manner can be distributed to family members, doctors, case managers, and others.

The monitoring and analyzing by system controller 110 and remote case monitoring system 148 also makes it possible to collect action priority information. For example it is possible to determine when users do not get out of bed. In addition it may provide an aggregate data base for identifying users requiring personal intervention. Additionally, it may be possible to provide a central hub for the collection and exchange of information with direct case management resources.

Local system controller 110 can be programmed to perform a variety of functions related to data base report generation and intervention decisions. In one embodiment of the invention system controller 110 can be programmed to learn activity patterns of the user. The leaning by system controller 110 occurs through analyzing sensor data and performing a variety of operations that change various parameters of the user. For example, timing and frequency parameters of expected activity events can be changed based upon a trend analysis of the past timing, frequency, duration and concomitance of events. The trend analysis can be based upon an interval of a week, a month, or other time period for which data is internally stored.

The learning of user activity patterns by system controller 110 or remote case monitoring system 148 can be accomplished using various techniques. In most of these techniques the learning process involves the changing of variable values, parameter settings and decision algorithms. The quantities changed in this manner are changed with respect to interpreting data derived by sensors for machine initiated interventions and the production of various reports.

The determinations of the system of the present invention are based upon the assumption that the best predictor of future behavior is past behavior and upon the empirical knowledge of the relatively invariant frequency, timing, and duration of essential activities of daily living as part of daily and weekly cycles. Using these bases, it is possible to use a variety of methods to determine whether the activities on a certain day fall within or outside of the range of statistically expected occurrences of the activities. In the preferred embodiment, the user monitoring system uses well known algorithms for analyzing continuous baseline data.

Variable values obtained by system controller 110 or remote case monitoring system 148 can be in the form of time and date stamped event data or transformations thereof. For example, the variables can be a count or a weighted frequency of occurrence of a predetermined measurement, such as the number of times within a predetermined time period a medication is taken or a toilet is flushed.

Using programming and statistical techniques well known and understood by those skilled in the art, system controller 110 can be enabled to learn the typical timing and frequency of a user taking each prescribed medication as well as the number of times that a user typically uses the toilet. Using such techniques it is also possible to learn the typical timing and frequency of the user opening and closing the refrigerator door, the silverware cabinet, the microwave oven, and the stove, as well as the typical time of getting out of bed in the morning.

Typical variable values used in the method of the present invention for the purpose of, for example, report generation and learning, can be understood in the common statistical sense of measures of a central tendency paired with an appropriate measure of dispersion. The measurement of the central tendency of sensor events can include measurements such as mean, median, and mode. The measure of dispersion can be measurements such as standard deviation and interquartile range.

There are various techniques for statistically determining a typical value of a measured event and then using this value to predict the value of future events. A common technique sets the typical value equal to its measure of central tendency bounded by a confidence level (sigma) equal to +/− the appropriate number of dispersion units to account for an alpha level of (typically) 0.05. For each measurement within an activity or event domain, these standard statistical procedures apply, especially as used in relation to continuous baseline or moving averages. For example, motion out of bed, the opening of a refrigerator, or taking a medication, controller system 110 may store this information and compare it with past similar events using well known statistical methods of determining whether it falls within or outside of the typical range.

For example, a waking time may be compared with thirty previous waking times by determining whether it deviates by more than two standard deviations from the arithmetic mean of the previous thirty waking times. This is one type of comparison of an individual data point with a baseline computed as a moving average of past events.

Controller 110 can be programmed to make decisions based upon comparisons of new event data with past event data such as this. For example, machine initiated interventions and special data transfers or reports can be generated if a user appears to sleep more than two standard deviations past the average waking time. In this case the trigger event is the lack of a signal from the sensor configuration used to establish that the user got out of bed. Thus, controller 110 need not remain programmed to expect the user to be awake at a predetermined time. Rather it can adjust and readjust the expected wake up time based upon the past sleep and waking patterns of the user.

In a similar fashion, system controller 110 can be programmed to permit the computing of average or typical expected values for any sensor based data or data derived from sensor based information. Programming controller 110 in this manner requires programming it to permit storing and updating of moving averages and sigma values for time, duration, and frequency of the activity and comparing the stored updated values to incoming data points.

System controller 110 can be enabled to change parameter settings in which variables are specified. For example, the number of medications within a medication regime can be increased from two to three on a daily basis. Using an additional position/compartment/switch provided on the medication monitor, the present invention can determine information for initializing a new variable associated with the new medication and begin recording time and date stamped information on its usage.

After several days, while the user takes the new medication, the average time and frequency baselines associated with the new medication become stable.

Simultaneously, the sigma level (per. eg. two standard deviations) tends to become smaller in terms of the number of measured units as the number of observations increases. This permits system controller 110 to detect errors such as taking too few or two many of the third medication in a given day.

Other changes in parameters that can be learned by system controller 110 are those associated with changes in meal preparation by the user. An individual user may have a pattern of preparing meals twice daily. For example, the user may normally prepare meals only in the morning and in the evening. The user may only rarely prepare lunch. The timing, frequency and duration of the sensor correlates of meal preparation change.

In principal, it is possible for the system controller to learn any pattern of repeated behaviors conveyed to it by a sensor capable of signaling the occurrence, non occurrence, time and duration of any activity event.

Activities of Daily Living: "ADL's"

ADL's (Activities of Daily Living/instrumental Activities of Daily Living) comprise those goal oriented activities which must be performed by or for a person in order to live independently in their dwelling. These include bathing, transferring, dressing, eating, grooming, meal preparation, light housekeeping, laundry, medication management, and other necessary tasks relating to personal care and household maintenance. We turn now to additional means for sensing and monitoring various activities germane to the current invention.

Toilet use can be monitored various sensor configurations. In the preferred embodiment, a motion detector and a flush switch detector are used in concert with a pressure sensor/position sensor combination on the toilet seat. The motion detector is placed in the bathroom and indicates the presence of individual(s) without regard to specific activity.

Bed-wetting can provide a problem requiring monitoring in a variety of situations. Bed-wetting can be monitored by means of moisture sensors placed under the on the surface of an under sheet pad on which the monitored individual lies.

Meal preparation may be monitored by means of a combination of sensors indicating the opening and closing of drawers, cabinets and appliances typically used by the client to prepare meals. In one embodiment, the refrigerator door, the silverware drawer and the microwave were monitored with reed switches to determine the presence, timing and duration of use corresponding to meal preparation. In an alternative embodiment, electric current flow detectors could be used to record the use of various appliances (e.g., coffee maker, toaster oven, etc.) used in meal preparation. Additional heat sensor configurations could be used to scan the stove. Pressure sensors, with or without weight differentiating means, could be used in the chairs at the eating table, etc.

For the current invention, variety of means have been developed to employ a small radio frequency transmitter and movement sensing trigger which can be attached directly to household objects thereby conveying to the system controller when these objects are manipulated. The preferred embodiment uses such an object movement detector (OMD) consisting of an inertia-momentum sensitive switch (mercury bulb or vibration detector) coupled to a transmitter with a timer/bounceless switch and timer reset which is small, low in current draw and which can be attached to the object. When the object is moved/manipulated, a pulsed RF signal is emitted which identifies the object and is received by the local controller and time and date stamped. Such a jiggle detector can be attached to brooms and hairbrushes, electric razors and assisted devices like walkers and reachers.

Eating can be monitored through the use of pressure pad sensors on tables and chairs and if need be the use of OMD's on silverware. Housekeeping can be monitored by placing OMD's on broom, dustpan, vacuum cleaner to react to manipulation. In principal, any ADL/IADL can be monitored by means of a configuration of sensors and this information transmitted to the local controller and integrated into the daily activity log for use by care providers or for machine initiated interventions such as reminders. Laundry activities can be detected using a current draw detector on a washer or dryer. The appliances' electric lines can be passively coupled to a current draw detector configured to transmit a signal to the local controller when they are in use resulting in time date stamp and duration data to be logged.

Grooming consists of a variety of behaviors, commonly inclusive of hair brushing (for women), shaving (for men). This affords the possibility to attach an object movement detector (OMD) onto the hairbrush, razor, and other grooming implements to signal the local controller when the grooming behavior is taking place.

Bathing can be monitored by several means. A variety of devices can be coupled to the plumbing to determine if water is flowing into the tub/shower. A water/moister detector can be placed in the tub or at the opening of the faucet/shower head to react to the presence of water flow without direct physical connection to the plumbing. A pressure sensitive switch in an insulated no slip mat at the bottom of the tub/shower could be fitted with an RF unit so when the individual steps or sits on the surface the information is conveyed to the local controller. Each or a combination of these methods could be used to determine bath/shower use and transmit sensor data to the local controller.

Dressing consists of a complex ensemble of tasks requiring both cognitive and manipulative functions. For this reason specialists in geriatric functional assessment regard dressing as a benchmark of overall functional health and the length of time it takes to get dressed as an indicator of level of functioning sensitive to changes in ability. Dressing can be monitored by placing reed switches on the dresser drawers and placing sensors in the closets can indicate the presence, time and duration of dressing activity.

Non-ADL Activity Monitoring

In addition to task oriented activities, there are repeatedly occurring behaviors which are both important to the individual's lifestyle and indicative of their normal behavioral routine. This behavior includes a range of sedentary recreational activities such as television watching, radio or audio entertainment usage, computer usage, book reading, needlepoint, etc.

Such activities can be monitored in various ways. Those involving the use of electronic or electrical appliances can be monitored by a variety of means capable of determining when the appliance is on or off. For example, a television can trigger a current draw detector or a photo diode mounted on the corner of the CRT display. The detector should be configured to send data whenever the television is turned on or turned off so that it would be possible to log the time on time off on a daily basis. Given the popularity of television and the relative regularity with which it is viewed by many people, it may be useful to use this data in various ways. For example, behaviors whose change can be monitored could include early and late television watching. Similar techniques could be employed in relation to CD, radio, VCR's, computers, etc. which could produce information indicative of normal daily activity.

For example, an individual may typically watch favorite programs in the afternoon between 2 and 5 pm Mondays through Fridays. This activity, while not directed toward achieving functional performance goals maybe nevertheless an important part of the typical or normal daily routine of the individual. Changes in television viewing routine patterns, for example not watching the afternoon shows or watching 14 hours of television continuously may indicate a change of activity rooted in a health, cognitive or other problems and therefore may provide very useful information for reporting purposes or interventions. The preferred embodiment of the monitoring system television use is monitored by means of a current draw detector. However, it is to be understood by those skilled in the art that many commonly used means of determining whether the unit is on or off can be used to send a signal to the monitoring system. Furthermore, similar techniques could be employed in relation to CD, radio, VCR's, computers, etc. which could produce information indicative of normal daily activity.

Distinguishing Among Several Individuals in Dwelling Unit

The present invention also includes means for distinguishing the activities of individuals in multi individual dwelling units. It may sometimes be useful to separately log the activities of two or more individuals living in the same household. In the case of medication adherence, this simply entails using separate medication monitoring caddies for each individual, each caddy signaling the local controller unit codes unique to the individual person being monitored. In the case of other activities, such as transference, toilet use, bathing, meal preparation, laundry and housekeeping it is necessary to introduce a variety of methods for distinguishing among multiple individuals and creating a separate activity log for each individual. Described below are a variety of methods that do not require the user to carry a special device on their person and rely entirely upon the individuals interaction with objects in their environment. Also described below is a special device, for example any type of transponder worn by the individual, which emits a very short range signal detectable used to detect the proximity of specific individuals to objects in their environment used in carrying out the monitored activities of daily living. In the preferred embodiment of the invention, the transponder or a similar device is not required for the system to work, but adds additional information to increase the validity of the determination of which individual is performing which task and when.

For transferring in and out of bed, it is possible to configure pressure sensitive switch pads on either side of the bed, on the floor, on the mattress, or both. With knowledge of who routinely sleeps on the right and who sleeps on the left, it is possible to configure these pressure sensors to indicate whether individual a or individual b is out of the bed.

For transferring onto chairs, it is possible to use a pressure sensitive sensor that responds to relative weight with sufficient precision as to distinguish between two individuals, such as a husband or wife. It may be possible to know which chair is customarily occupied by which individual, especially in relation to a married couple.

For toilet use, the above described differential weight sensor could be installed in the toilet seat along with a tilt switch sensor to indicate when the seat is in the upright position (customary for male urination) or in the downward position. Additionally weight sensor pads could be embedded in a 'bath mat' in front of the toilet to assess weight differential. A variety of techniques could be used to signal toilet flushing, such as a flotation switch connected to an signaling unit such that when the water level in the tank drops below a threshold level, a the normally open float switch closes.

For bathing, a waterproof version of the weight sensitive bath mat could be placed in the bathtub to determine the differential weight of the person.

With respect to differential weight, in most case it is useful in a two individual household and the weight threshold should be adjusted to approximately the mean of the weight of the two individuals. Given the possibility that either individual may loose weight over time (or gain which is rarer) and the two weights become close to equal, it may be necessary to repeatedly weigh the individuals. This can be done unobtrusively using any known methods or just by wiring the scale and reminding the individuals to weigh in using his/her scales or transponders or some other means for differentiating the weights.

Physiological Measuring of Health Conditions

The monitoring of health conditions among individuals in their dwelling units consists of monitoring both their activities and their physiological functioning. A wide variety of physiological functioning measuring and monitoring devices are available for home use as variables, including, but not limited to, body temperature, pulse rate, weight, blood sugar, blood pressure, and oxygenation. All of these devices, such as infrared temperature, blood sugar and pulse readers, are currently available with digital readouts and could be easily modified to transmit the information to the local controller so that these physiological data could be recorded along with the activity data and integrated into a single report combining both kinds of information for family and professional care givers as well as for triggering machine initiated interventions. Many devices for taking measurements usable in accordance with the present invention are taught in Alyfuko, U.S. Pat. No. 5,410,471, which is incorporated by reference herein.

Furthermore, the system of the present invention can assist users in the measurements. For example, in order to determine blood pressure a user can be instructed by the system to be seated, put on the cuff and perform other required steps. If the readings obtained are not within predetermined ranges, the user can be instructed to repeat to the measurement. This can be done by interactive software on the user's PC or by way of the internet.

An example of readings indicating intervention could be if a person is showing an trend toward decreased activity during the day and is not sleeping in bed at night. This can reflect symptoms of congestive heart failure (CHF). In this case decreased activity may be measured as fewer total movements around the house, fewer total movements going in and out of the dwelling unit, less frequent or slower (longer average duration) stair climbing (where applicable), and/or longer sleeping hours. The local controller could be programmed to trigger an intervention in view of decreased activity and/or not sleeping in bed at night, which would entail a request/reminder for taking a blood pressure reading during the next day. It could also plot the blood pressure against a continuous baseline of previously taken blood pressures, and, if either diastolic or systolic pressures fall outside of upper and lower critical values (sigma levels), action could be taken informing the monitored individual, their physician and/or other appropriate persons of a possible change in health status. Instructions to seek checkups or contact care providers can be the interventions indicated by the reports of the present invention.

When the physician compares the blood pressure data, activity log data and medication compliance data within an integrated health and functioning report, they are provided information invaluable for making adjustments to therapy. For another example, frequent over night bathroom use may indicate the presence of an infection. By combining information about toileting and body temperature readings in a single report, the physician or other care giver could be informed of evidence of an infection and make sure that the monitored individual is quickly seen by the appropriate providers. Again, it is possible to program the local controller to take action based on behavioral changes, physiological changes or a combination of the two. For example, the local controller may be programmed to request that the monitored individual take temperature and blood pressure or other measurements after night of unusual bathroom or other activity. In principal, any combination of physiological measuring devices can be integrated into the system by equipping them with a compatible RF transmitter and enabling these devices in the software.

In the various embodiments, the monitored individual is asked to participate in periodic automated check ups during which time they are reminded and prompted by the local controller to sit down at a table, take their temperature, take their blood pressure, etc. The controller prompts them using a synthesized or recorded voice that can be heard through speakers connected to a personal computer wherein the microprocessor of the local controller resides or a speaker phone connected to the local controller in the form of a stand alone unit. The individual is thereby instructed on what to do during the check up. The data captured by the controller is analyzed against the continuous baseline average and the results reported to the remote monitoring site. Thus the present invention permits the integration of information with respect to physiological and behavioral measures into a single report for human end users and/or machine initiated interventions.

Portability

While the current invention consists of various means for monitoring individual user or users in a dwelling unit, there is no reason why portable appliances could not be incorporated into the system. For example, a portable medication monitoring device could be carried by the user out of the home. This device could be enabled to record and/or remind the individual to take their medications. Upon returning to the dwelling unit the medication unit is able to communicate by RF signaling to the local controller and information about medication taken outside of the dwelling unit is integrated with the information about medication taken that was collected in the dwelling unit. Thus it would be possible to integrate information about medication taking behaviors of the user outside the dwelling unit with the information obtained within the dwelling unit to develop a more complete picture of the individuals daily behavior.

In addition to portable medication monitoring, it is possible to have portable physiological monitoring (e.g., heart, respiration, blood oxygenation, blood pressure, etc.) and/or activity movement monitoring (e.g. odometer, walking odometer-like device, etc.) Likewise, similarly to the above described portable medication monitoring, it is technically easy to create data transfer channels and links integrate the signal data gathered from the portable units within the home-based local controller and use this as the basis for the production of daily living reports for human and machine use. Such reports and information products might prove very useful to maintaining the health and functionality of users.

Security and Environmental Monitoring

In addition to goal oriented functional activities and other behaviors which make up the routine everyday activity of individuals, the monitoring system of the present invention is capable of collecting and analyzing information relating to security, safety and environmental concerns within the dwelling unit. As described above, various embodiments of the monitoring and report generating system maybe used to log activities relating to dangerous appliances, such as the stove, and, necessary, to take automatically initiated action in the event of a problem, such as shutting off the stove if it is determined that it has been left on too long or in the event that smoke or heat detector has been triggered.

Also described above are means and procedures for monitoring bathtub overflow, and in a similar manner, overflow of sinks in a dwelling unit Both of these functions focus on detecting events that, if unchecked, may have serious negative consequences to the safety of the monitored individuals and/or the condition of the dwelling unit. In addition to these functions, there is a wide range of additional events impacting the security and safety of individuals and their dwelling units, which may prove very useful. For example, monitoring the closing and locking of the door leading outside of the house or apartment, along with reports and reminders, would reduce the risk of security problems for many individuals. Forgetful or disoriented individuals may be particularly helped by such a function. The monitoring of door closing and locking could be accomplished by a standard magnetic reed switch which opens and closes a circuit causing signals to be sent to the local controller in conjunction with a switch configuration fitted to the locking mechanism in such a manner as to enable the detection of the state of the locking mechanism as being either locked or unlocked. This switch would then be connected to the appropriate signaling device to convey information to the local controller so that the monitoring system could integrate this information into various reports and intervention decisions.

Ambient temperature above and below healthful levels is a real threat to the health and well being of frail elderly populations in particular. Each year heat waves and cold snaps kill scores, if not hundreds, of older people in part because of their physiological inability to adequately judge extreme and dangerous variation in ambient temperature. Many temperature detecting units, with either electronic or mechanical thermostatic components, are familiar to those skilled in the art of environmental control. Such units are commercially available and routinely used in the monitoring and control of heating and cooling of buildings. By connecting temperature sensors to the appropriate signaling system, room temperature data can be transferred to the local controller, logged, analyzed and serve as the basis of machine generated reports as well as interventions. In the preferred embodiment of monitoring system, temperature sensors are used to trigger alerts and, if need be, automatically initiated communication with care givers if the temperature rises above a high threshold or falls below a low threshold. This functionality can save lives.

In principle, the information from security and environmental detectors can be integrated with the behavioral data within the local controller and be used, in conjunction with the behavioral information, to enable a variety of interventions. For example, the system could be configured and programmed to sense that the front door is unlocked, to note that there has been no movement in the dwelling unit since the door was shut, and take action by automatically locking the door. A variety of algorithms are possible for making interventions based on a combination of security and behavioral data.

Similarly, temperature data could be used in combination with behavioral information to inform analysis and interventions. For example, an increase in the amount of time an individual stays in bed along with the information that the room temperature has fallen below 50 degrees may be useful information to family or professional care givers who need to take quick action to help the individual. As with door locking and physiological measurements, there is no reason why environmental variables such as temperature could not be integrated into the reports and interventions of the monitoring system. Other environmental variables may include, smoke and particulate dust detectors (such as an optical smoke detector would measure) noise and vibration, carbon monoxide, humidity, etc. Any environmental condition that can be automatically detected using sensors could be used in connection to the monitoring system here described.

Internet

The use of the internet as a means of communication between the local controller and the remote monitoring site not only makes use of an efficient and cost effective means of exchanging information but also affords the possibility of multiple users and various types of individual and institutional users to access report information posted by local controllers to a website. In one embodiment, a number of local controllers use a modem and automated dial up software to post activity logs onto a website using email as the means of data transfer. The posted email is then subject to interpretive post processing, converted to a variety of summary reports for different users. For example, relatives of the monitored individual may access the website, type in a pin number or password, and for access a report about basic day to day activities. Or a physician group at a hospital could access the website using and institutional portal and be able to get a report on medication adherence in greater detail than that available to the monitored individual family members. The remote monitoring station with its website could also be programmed to store and process financial and billing information relating to the access fees and report request transactions for the various individual and institutional clients. For example, family members might pay a relatively low monthly fee for monitoring and a small transaction fee for each report accessed while a health provider system right pay a substantially higher per month fee and report fee. Billing can be done by the remote monitoring site computer along with the above discussed processing and transfer of activity information on the monitored clients.

Whereas the internet provides excellent means of exchange of information in non emergency situations, it may be useful to couple the system to a pager to call helpers and family in case of an alarm code. For example, if a monitored individual does not get out of bed before a critical time lapse, paging can be done in conjunction with or in place of phone calls. Using alphanumeric display technology common in pager systems, the nature of the possible emergency can be designated using ASCII codes in place of the synthesized voice used on a voice telephone.

The internet can be used as a means of information transfer between local and remote controllers for any purpose. For example, the local controller can dial up an internet service provider (ISP), log on, and send or receive packets of data for purposes of analysis, intervention, report writing, reprogramming, etc. The remote monitoring site, structured as a web page, can store, analyze and disseminate a wide variety of user reports in various ways. In one embodiment, the local controller is programmed to access the internet periodically (e.g. every 6, 12, 24 or other number of hours) and transfer data to a remote site in the form of web server. The remote monitoring site receives the information and makes it available to the client, family, professional care givers, case managers, health care providers and others who can access this information by logging on and entering secure portals using standard identification and password protocols. This enables a wide variety of users to make queries of the reports, analysis and records based on the monitored client(s).

Figure 12:
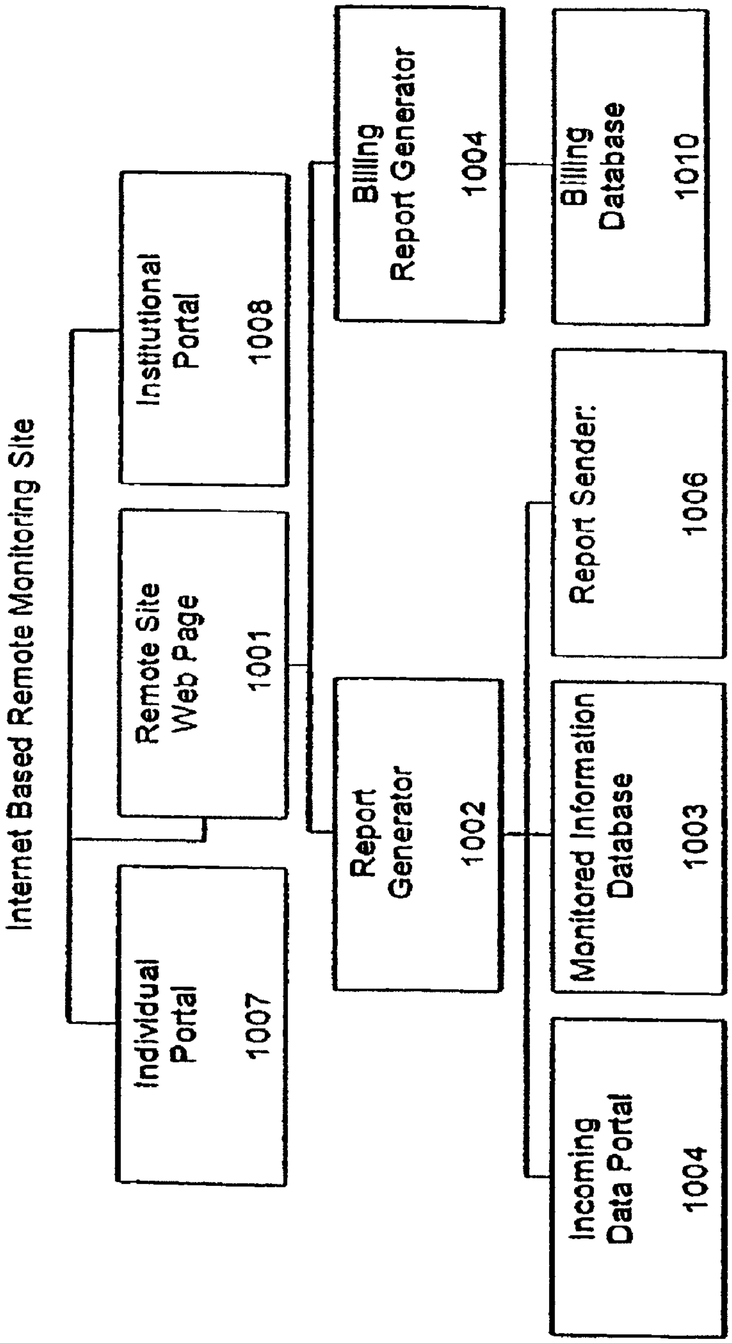
FIG. 12 is a block diagram representation of the user monitoring system of FIG. 1 wherein the internet is used as the communication channel.
Figure 13:
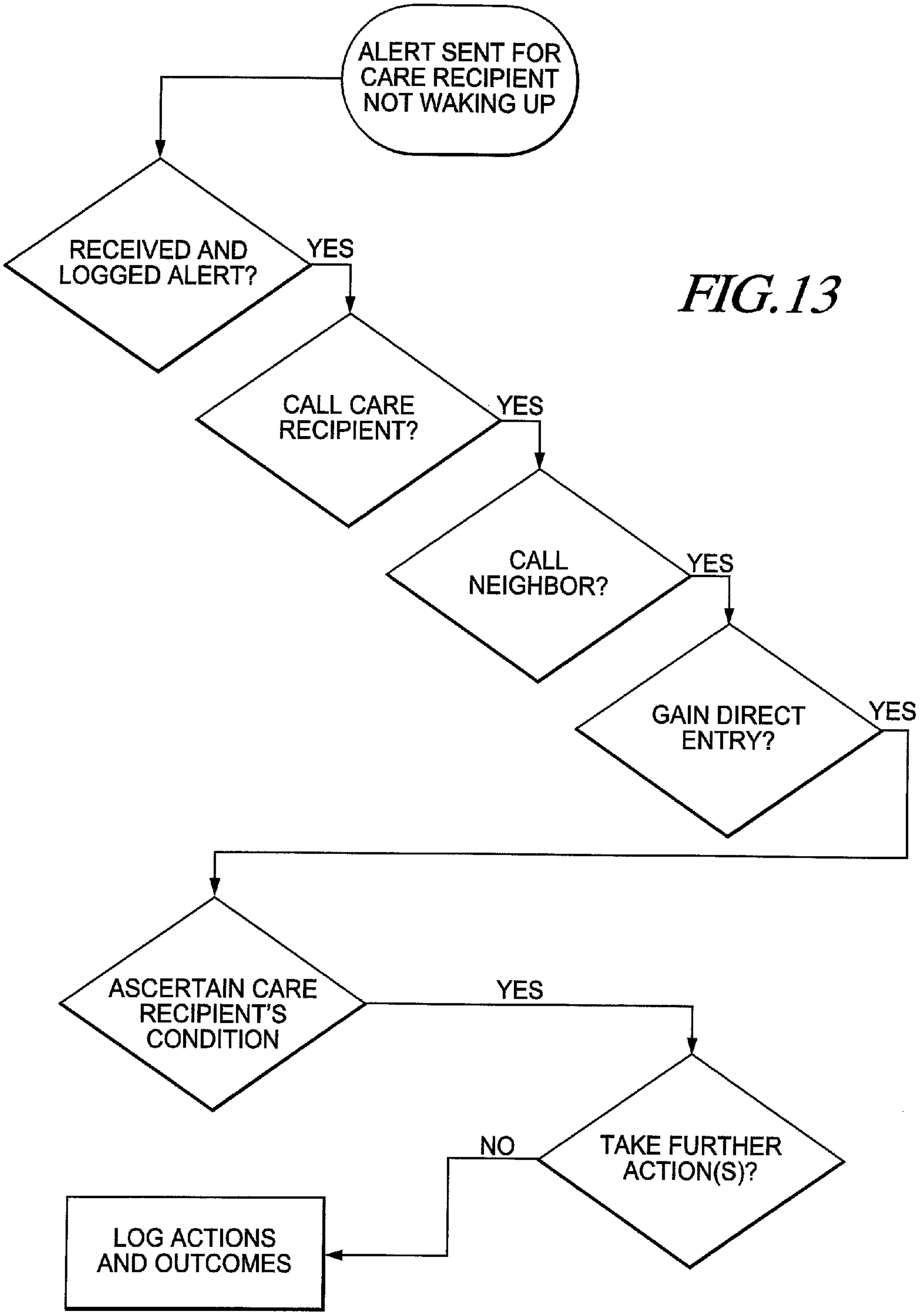
FIG. 13 is a flow chart representing operations performed by a caregiver in response to the detection of an event.
Figure 14A:
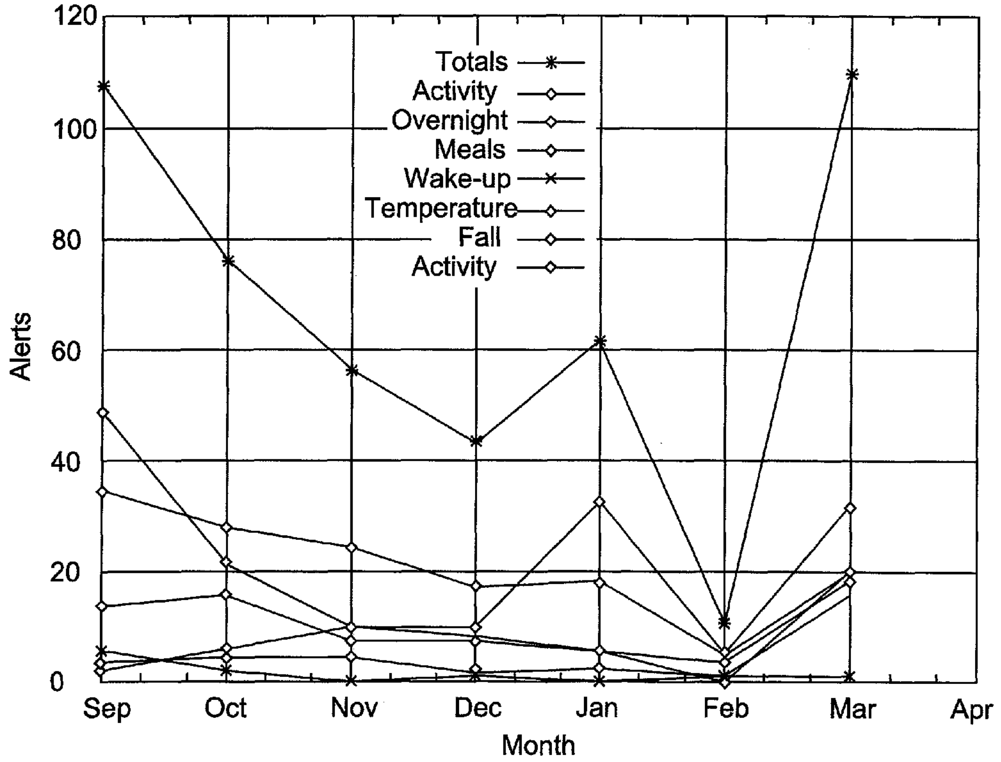
FIGS. 14A, B show client summary page alerts according to the present invention.
Figure 14B:
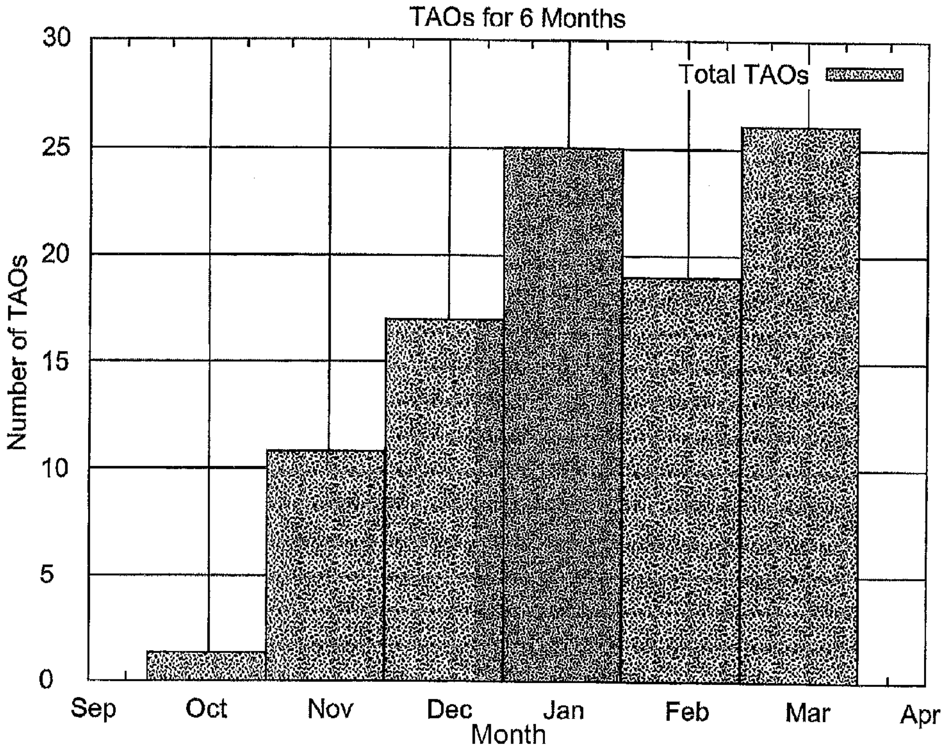
Figure 17C:
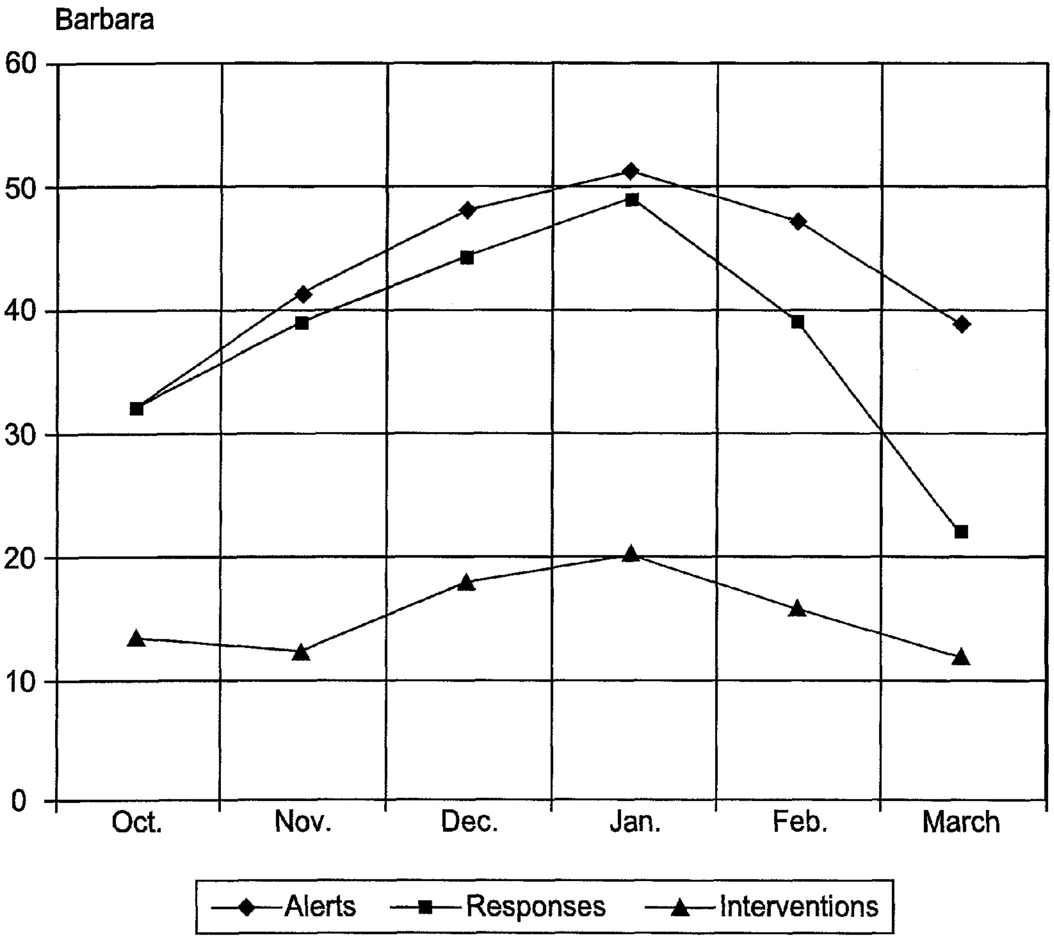
Figure 18A:
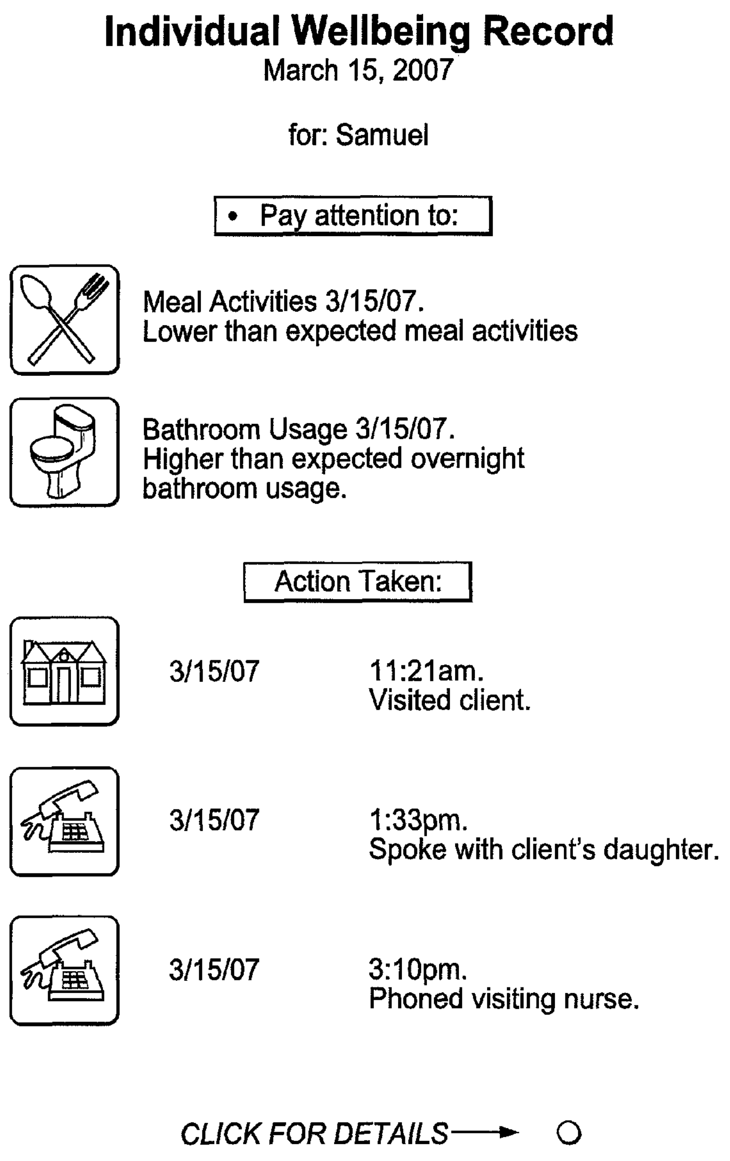
FIGS. 18A-D show an individual wellbeing record.
Figure 18B:
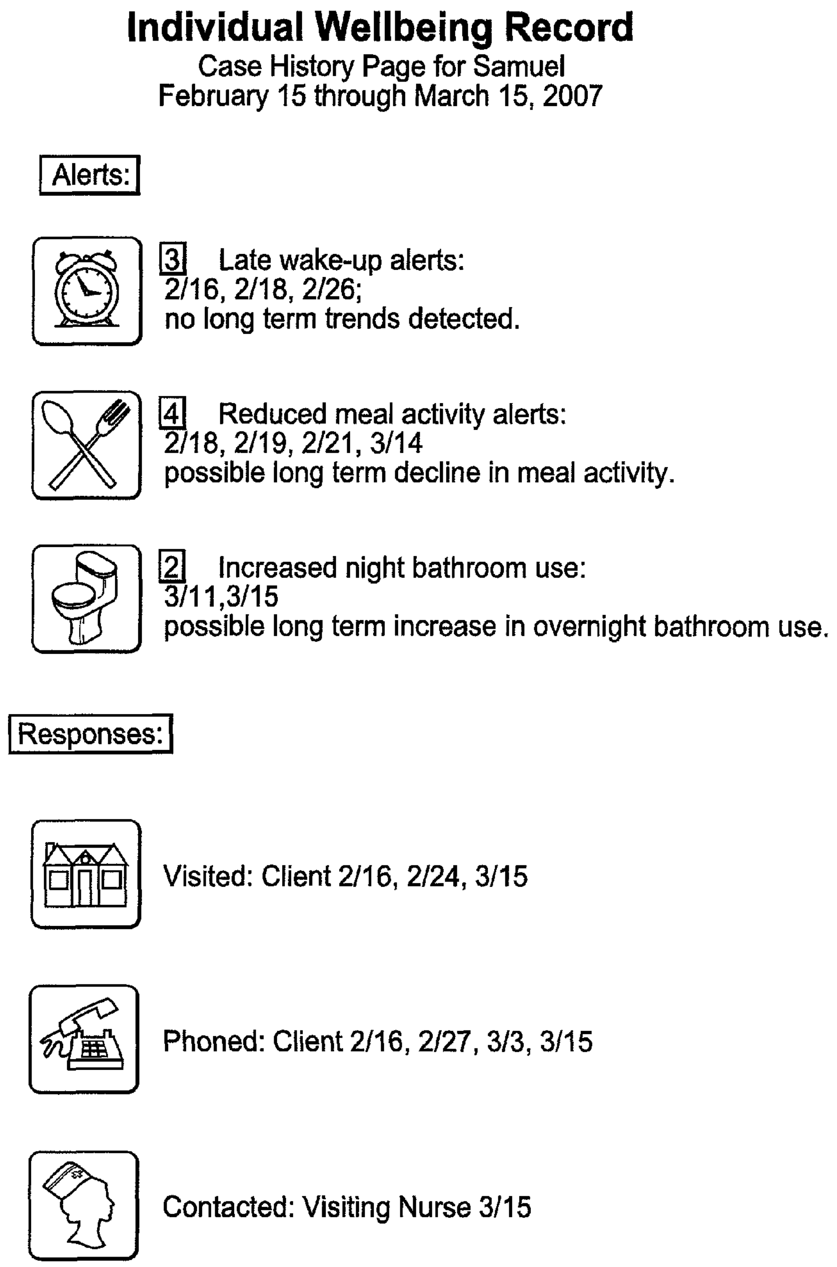
Figure 18C:
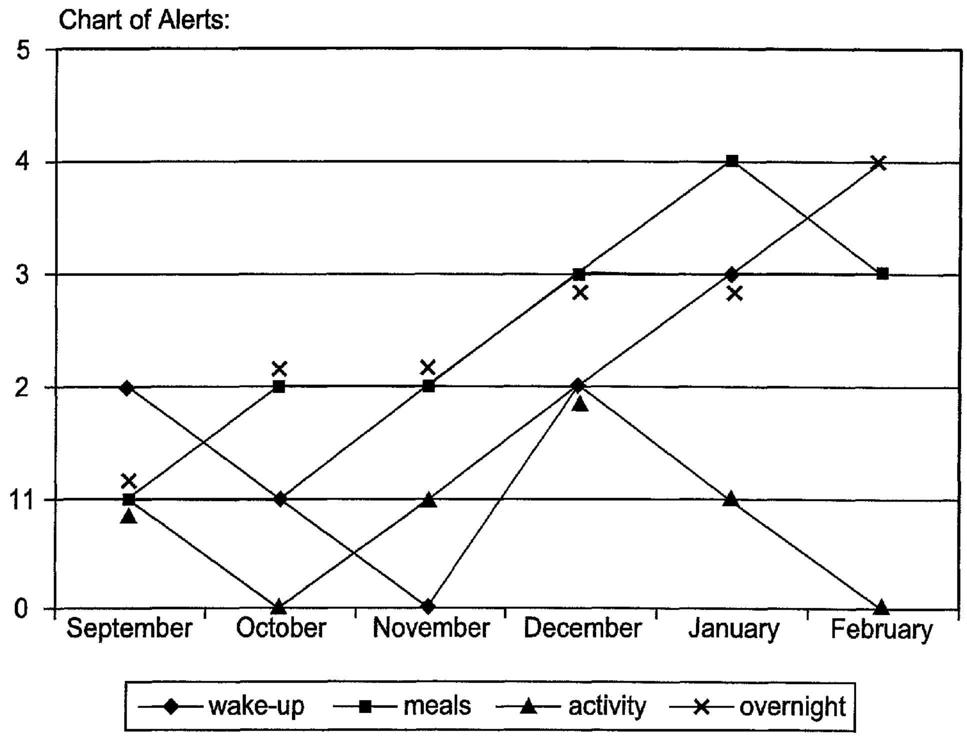
Figure 18D:
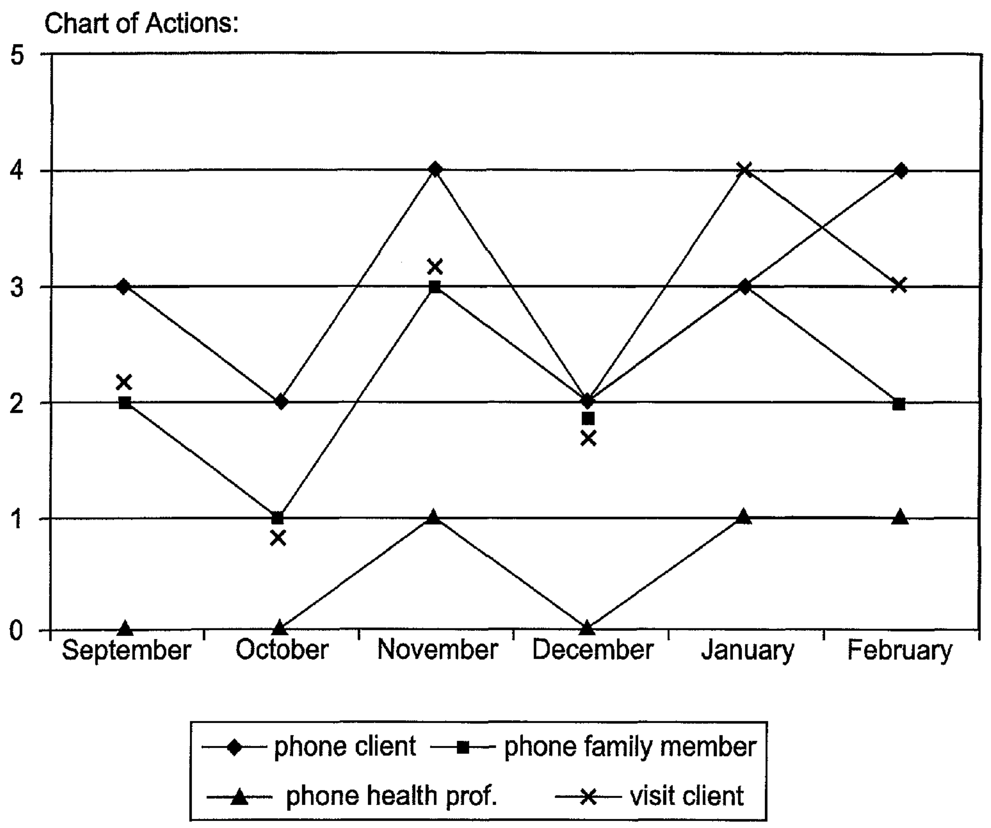

Furthermore, the plurality of user portals by which clients: (i.e., monitored individuals), family members (informal care givers), health providers, social support agencies (formal care givers), can each access client information at will could be used to automatically create a transaction record usable for information tracking and billing purposes. FIG. 12 below illustrates an embodiment of an internet web site with multiple user portals. In this way, clients and other subscribers can be tracked and billed for information accessed in a wide variety of ways. In one embodiment, clients, gain free access and registered family members can make a number of included queries per month with a per query charge thereafter. Hospitals can also be charged a per query fee.

In addition to placing client information on a web server and allowing registered users to access the information, it is also useful to periodically transfer information and reports to subscribers via e-mail. Thus family members, physicians, case managers and others can receive periodic machine generated reports on the client (daily, weekly, monthly, etc) via email which may be received on one's computer or any other device capable of receiving email messages. In addition, emergency or quick response options for information transfer via the internet are afforded by linking the internet with a wide variety of wireless devices, including, but not limited to cell phones, pagers and personal data assistants. For example, if a monitored individual does not get out of bed before a critical time lapse, paging can be done in conjunction with or instead of phone calls. Using alpha numeric display technology common in pager systems, it would be possible to designate the nature of the possible emergency using displayed printed words in place of the synthesized voice used on a voice telephone. The lining of local controller 100 and the remote monitoring site via internet as a communication channel need not alter the essential features of the local controller and remote monitoring site. The local controller can be used for obtaining, storing, organizing and analyzing sensor based data in the dwelling units of the monitored individuals. As mentioned above, it is possible to configure/program the local controller to carry out many of the functions of the remote monitoring site. Thus a wide variety of embodiments with differing amounts of functionality distributed among local controllers and remote monitoring systems are possible. In principal all functions of report generation, automated behavioral and physiological profiling, machine initiated reminders and interventions can be carried out for individuals within a single dwelling units by the local controller. It is therefore possible to greatly reduce the number and complexity of functions of the remote monitoring site as long as an end user receives information about the client from this site.

In one embodiment the remote site is reduced to a pager, phone or radio receiver, which signals care givers and others when the client is in need or reports information via synthesized voice or displayed text. In this case the functionality of the local controller is maximized and the remote monitoring site minimized. On the other hand it is possible to have a monitoring system configured whereby sensors are placed in a dwelling unit and the local controller consists of no more than a system for gathering their outputs into a usable communication channel which then is processed by the remote monitoring site. This would be a minimalized local controller dependent for data analysis functionality almost entirely by the remote monitoring system. In the preferred embodiment, higher level functions of case management pertaining to the collection and analysis of data on single or many individuals in single or many dwelling units are carried out by a remote monitoring system whereas local controllers function primarily to log, analyze, report and make automated inventions based on sensor data within a single dwelling unit and the local controller is in the dwelling unit and that the remote is not.

The ubiquity of the internet makes it a preferred means of communication link between the local controllers and the remote monitoring site. There are various means of transferring data to, through and from the internet known to those skilled in the art. In a preferred embodiment the communications link between local and remote monitoring sites can be established and maintained by email. The activity log is simply uploaded as a text file and mailed to the remote site, which receives it, places it in the correct mailbox, processes it and then may automatically send out reports via email to end users (e.g., family, physicians, social workers, etc.), or posts reports on a secure website accessible by password to family and professionals.

Referring now to FIG. 12, the preferred embodiment of the internet based remote monitoring site is organized in the form of a web page 1001. Webpage 1001 allows clients to access information about the monitored individuals by means of client portals. Two portals are shown. The individual portal 1007, allows the monitored individual and designated individuals (such as family members) to access the behavioral and other information which is accumulated and integrated by the local controller and transferred to the internet by any variety of commonly used means. The institutional portal 1008, allows for institutions (e.g., health care providers, case management service units, insurers, etc.) to access information about monitored client). In the preferred embodiment these portals make use of commonly employed means for assuring security of the information about individual clients such as the use of PIN numbers, encryption, firewalls, etc. to assure that only authorized parties are able to access secured information. In principal, any number of portals could be used to accommodate different groups of clients with differing access to information.

A report generator 1002, a data base of monitored information 1003, and an incoming data portal 1004 form the means for generating a wide variety of reports from data accumulated by the local controller. The incoming data portal 1004 receives packets of information from any number of local controllers. In this embodiment, e-mail serves as the means for data transfer wherein the incoming data portal is configured to receive from the monitored individuals. The data base of monitored information 1003 contains a client background record of each monitored individual which includes demographics, medical and functional needs, plus billing information (e.g. postal address, phone number, etc.).

With respect to the data coming in from the incoming data portal 1004, the data base of monitored information 1003 also sorts and stores data files for each individual local controller, automatically updates the data base with newly received, information and maintains an a record of instructions which determine the form, content and receiver of reports to be generated by the information. These instructions include, but are not limited to, the type and number of monitored events to be included in a given report, the particular type of summary used within the report (counts, sums, averages, critical levels, verbal descriptions of events, graphical descriptions of events, etc.), the frequency of the reporting period (hourly, daily, weekly monthly, etc.) as well as information pertinent to the receiver of said reports (name, relationship, e-mail address, phone/pager numbers, postal address, etc.).

In this way the data base of monitored information 1003 includes the local controller accumulated data plus additional information about the monitored individual, the reports to be generated, and the parties to receive these reports. At time intervals determined in individual record instructions contained in the data base of monitored information 1003, the data is processed through the report generator 1002 wherein a variety of reports are produced reducing the data collected by the local controller to numerical, graphical and written reports. These reports are then saved transferred to the report sender 1006 which can sort, store and transfer the reports to a variety of end users by means including e-mail, automated or live human telephone calls, voice/alpha numeric paging and postal mail by means of printing the report on paper and physically sending it to the appropriate customer. Any single or combination of commonly used means for conveying numerical, graphical and written information can be used.

The preferred embodiment uses e-mail for non-priority reports and paging and telephone messaging for priority reports/alarms. Billing report generator 1010, billing data base 1005 together provide a means for tracking customer billable usage of reports and queries. For example, each query from a family member may be tracked, a per query cost total tallied, and an end of the month usage statement produced which can serve as the basis of a bill. Similar procedures could be in place for institutional customers: a hospital may contract for 1,000 queries a month, pay a set amount, and then pay an additional amount per query when the contracted number is exceeded. The operation of billing report generator 1010 and billing data base 1005 require linkage to the monitored client data base 1003 so that information about the form and content of the reports, as well as customer and client information could be used to develop the billing reports. In addition, linkage with the report sender 1006, especially in so far as it sends reports by post mail, would be useful as a necessary means for printing and distributing the bill at the end of the billing cycle. Using means commonly employed in automated and semi automated billing systems, it is possible to configure the data bases in a number of ways with billing report generators to accurately and efficiently generate bills for services provided.

The above description of the internet based remote monitoring site also includes functions for reprogramming and maintenance of the local controllers 110. The previously described reprogramming function is capable of resetting parameters controlling data collections and interventions, as well as testing and status checking of local controller and its network of sensors. Such functions may prove useful if not essential in the development of various installations of the monitoring system.

It should be pointed out that any functionality described above as embodied in the monitored client data base 1003 could in a given embodiment be located in the report generator 1010 and that any functionality described as part of the report sender 1006 could in actuality be located in the report generator 1002 or monitored data base 1003. In principal, it makes no difference where the functionality is embodied relative to the conceptual block diagram, as long as the functionality exists.

Monitoring Caregiver Performance

Various health and wellness monitoring systems have been devised to collect information regarding the physiological, environmental and behavioral status of individuals for use by caregivers. Telecare, telehealth and social alarm systems are known in the art and have been implemented around the world with the intent of efficiently providing the right care by the right person at the right time. Telehealth systems using video/ audio conferencing technologies along with standard clinical tools such as blood pressure cuffs and thermometers have allowed health professionals to carry out “remote” visits to their patients. Social alarm systems have been deployed to establish urgent communication between a monitored individual and a remote care center enabling quick response in emergency situations. Passive actuation of such alarms (not requiring the monitored individual to physically send the alarm) is taught in various references and is implemented in numerous working systems (e.g., Tunstall fall and smoke detection). Monitoring of a person’s behavior, including goal-directed functional activities of daily living, has been taught and tested and in some cases commercialized, as in the case of U.S. Pat. Nos. 5,692,215 and 6,108,685 issued to the inventors of the instant application.

All of these systems provide actionable information for care professionals and family caregivers about the status of the monitored individual. Actionable information, whether in the form of telephone calls, call center alarms or web-based reports, can only be useful to caregivers if it is in fact used by caregivers. Furthermore, said information on the status of the monitored individual can only be reliable and valid information within the caregiving process if it is properly and adequately received interpreted and acted upon by the persons and organizations providing care. Put otherwise, even perfectly accurate information about the status of the monitored individual can have no positive impact on the delivery of care if the caregiver never receives it, interprets it, and does not take appropriate action in response to it. For this reason the actions of the caregiver(s) determine the effectiveness of behavioral, vital signs and environmental extreme monitoring as much if not more than the design and implementation of the hardware and software of the monitoring devices and systems.

With reference to FIGS. 13-18D, given the centrality of caregiver actions in determining the effectiveness of monitoring systems as tools for better care provision, it would be very useful to monitor the actions of the caregivers to assure the quality of these actions. In the most rudimentary sense, the monitoring could include the recording of caregivers receiving the information from the monitoring system(s), the logging of their interpretative actions as they determine the present status of the monitored care recipient, the tracking of actions taken by the caregiver(s) in response to their client’s status, and finally, the ability to register the impact of these actions on the client’s care in terms of alteration of a care plan or other interventions in a data base for the purpose of producing a variety of reports and analyses relating quality and quantity of care delivered and received in the caregiving process.

The preferred embodiment of the present invention combines information such sensor-based, objectively derived information with information entered into a care tracking data base by persons using keyboards, computers, PDAs, etc. in order to produce an integrated electronic Wellbeing Record. Such a record can track care delivery and provide the data for generating a variety of analytical reports as well as initiating a variety of machine initiated and human initiated interventions. In particular, the Wellbeing Record can be used to provide information such as continuous baseline assessment information and evaluation of the changing status of the care recipient in relation to specific care actions provided by professional and family caregivers within, but not limited to, the following seven domains: (1) tracking changes in care recipient outcomes; (2) tracking changes in care delivery practice; (3) analyzing individual outcomes for client wellness; (4) analyzing systemic/organizational outcomes for caregiving effectiveness; (5) assessing cost and cost benefits of caregiving actions for paid services; (6) assessing the effectiveness of specific care actions and interventions for individual care recipients in terms of client wellness outcomes; and, (7) assessing the effectiveness of specific care actions and interventions in terms of determining the most effective caregiving actions.

Taken together these domain related functionalities can provide informatics templates to enable the effective use of various telecare and telemonitoring tools within a care delivery system by continuously providing feedback about the effectiveness of ongoing care provision both on the individual and organizational level.

Core Functionality

The Core Functionality of this invention resides in recording and analyzing the actions of caregivers in response to alerts generated by a variety of telecare systems and/or information about the status of one or more care recipients gathered by traditional non-telecare means.

With respect to telecare applications, the preferred embodiment of this invention makes the following ten determinations are made in connection with the actions of the caregiver; 1) Has the caregiver received the alert?; 2) Has the caregiver recorded receiving the alert?; 3) Has the caregiver taken an action or actions?; 4) What actions have been taken by the caregiver and in what sequence?; 5) Does this sequence of actions follow the caregiving protocol?; 6) What is the decision tree map of the actions taken?; 7) How do the actions deviate from the specified (i.e., etic) caregiving protocol?; 8) Do the actions conform to the past actions taken by the caregiver?; 9) Do the actions conform the past actions taken for the client by their caregiver(s)?; and, 10) Do the current actions conform to the actions taken by the specific caregiver for the specific client?

The determination as to whether the caregiver has received the alert is accomplished by recording the opening and reading of the alert by the caregiver. This may be done by automatically logging the opening of a webpage on the caregivers pin secured portal corresponding to a specific alert, for example, an alert that a user may have not arisen out of bed after a threshold time of day. In addition, the caregiver is prompted to record an acknowledgment that they have received the alert. In the preferred embodiment, the caregiver may simply check a checkbox to indicate any and all alerts they are responding to at the time of intervention. This information is recorded into the Wellbeing database for further analysis, including, but not limited to a counting and statistical analysis of the number, types and contexts of alerts that are responded to and alerts that go unheeded.

The determination as to whether the caregiver has taken action(s) in response to the alert is accomplished by having the caregiver record each action taken as the response(s) is/are carried out. In the preferred embodiment the caregiver interacts with graphic interface which presents a combination of “radio buttons” and checkboxes to record the actions taken. For example, if the alert indicates that a care recipient did not get out of bed, a highlighted icon is presented to the caregiver with the image of a telephone and clicking on this icon initiates the dialing and/or records the fact of calling the care recipient to determine if they are in need of assistance.

A second means or recording whether a caregiver has taken action is to gather information from a variety of sensors at the dwelling unit of the user, including a sensor based means for determining if the caregiver is present in the dwelling unit at the time of the caregiving actions. In the preferred embodiment, the caregiver might wear radio frequency identification (RFID) device configured to trigger the local controller and record the start and ending times of the presence of the caregiver. In this way it is possible for the system to passively obtain information on the caregiving action. Depending on the nature of the caregiving process and the sophistication of the sensor arrays and context aware computing, embodiments of this invention my employ a variety of accelerometers, video image processing, vibration analysis techniques to further determine the specifics of the actions of the caregiver in addition to whether or not they were present at the care recipient's dwelling unit and for how long.

The determination of specific types of caregiving actions and their temporal sequence is accomplished as well by a combination of active data entry on the part of the caregiver and passive, sensor-based data collection. On the one hand the caregiver may enter via keyboard, mouse clicks and/or PDA screen what actions they are taking in the order in which they are occurring. On the other hand, sensors in the dwelling unit of the user give additional information about the sequence of events taken. For example, in determining the occurrence of a home health aide showing up at a particular time in the morning to help the user out of bed and into the bathroom, it is clear that the behavioral monitoring system described in Kutzik et. al. can be used to determine whether or not the home health aide carried out their assigned tasks and even be programmed with rule-based algorithms to send out alerts in the event that the particular timing and sequence associated with actions of a home health aide does not occur (per e.g., the sensor-based "footprint" of entry at front door, proceeding through the hallway to the user's bedroom followed by a minimum number of minutes of activity in the user's bedroom as specified by a moving historical average of the number of minutes so spent over a selected number of previous days, etc.).

In principal, footprints of complex caregiving actions can also be constructed and detected using sophisticated arrays of sensors. For example, a nurse may enter a patient's room, her presence indicated by rfid. She then takes the blood pressure, temperature and proceeds to carry out the sequence of steps necessary to change a bandage on a wound. Using wrist worn accelerometer units and video cameras with a variety of automated image processing techniques, it is possible to establish the timing, sequence and duration of the skilled medical care delivered. Furthermore, in so far as the nurse records her actions and the patient outcomes on her PDA, the information from the objectively derived sensor data can be compared with the nurse's account of her actions.

It should be noted that, depending on the particular caregiving protocol, i.e., the rules governing the actions of the caregiver in response to the needs of the care recipient, there may be considerable variation in the proportion of objectively derived sensor-based information versus information inputted by persons. In principal the procedures here described should be able to operate in any configuration ranging from all of the information coming from sensor-based remote monitoring devices to all of the information resulting from human data entry.

Caregiving Protocol: Etic and Emic

A caregiving protocol consists in the set of rules followed by family caregivers and/or professional caregivers that govern the sequence of actions taken in providing care to the care recipient. In the case of family caregivers, this is typically an informal or "emic" protocol, neither written down nor officially sanctioned as the correct set of procedures. On the other hand, the caregiving protocols of provider organizations employing professional and paraprofessional caregivers of various types (e.g., visiting nurses, occupational therapists, social workers, home health aides, etc.) are typically codified, officially sanctioned, and to some extent monitored as part of quality assurance and supervisory functions of the organization.

In the preferred embodiment of the present invention, the caregiver alert-action-response tracking system protocol would require that the caregiver respond to all alerts from behavioral and/or vital signs monitoring system by following a predetermined care action-response decision tree. Such a decision tree spells out the sequence of actions and contingencies of what a caregiver is supposed to do at each step of the caregiving protocol. Using a "wake up" alert as an example, the following illustrates the operation of a caregiver protocol.

A caregiver is sent one or more email, text message or cell phone alerts indicating that the care recipient has apparently not gotten out of before a time that triggers an alert condition. As soon as the alert is received, the caregiver is required to acknowledge receipt of the alert. Next the caregiver is required to call the care recipient. If this phone call results in user answering the phone, a series of questions are asked to see if they are in need of help. If the questions are answered in the appropriate manner, the sequence of caregiving actions may end. On the other hand, if this phone call to the care recipient goes unanswered, the caregiver is then required to call a designated person who may directly check on the condition of the care recipient, perhaps a neighbor with a key. Failing this contact, the caregiver may be required to personally attempt direct entry into the user's dwelling to make sure they are alright. Depending on the specifics of the caregiving protocol, the caregiver may be required to call 9-1-1 to gain entry into the care recipient's dwelling unit.

At each step of this protocol, the caregiver is presented with a set of choices. These choices may reflect relatively simple protocol responses to alerts, as above, or may be much more detailed and complex, such as those involving multi-stage skilled medical interventions. But in all cases the protocol can be represented as a decision tree "map" or flow chart like the one in the drawings. In the preferred embodiment of the present invention, the caregiver may be presented with a list of choices as "prompts" on a device interface in textual and graphical form enabling them to see which choices are available within the constraints of the protocol at each step of the process.

In the preferred embodiment of the present invention, it is possible to automatically make use of a decision tree map by entering the sequence of protocol instructions into the database and analysis software such that any given sequence of actions taken by the caregiver can be compared with one or more caregiving protocol maps to determine conformity and deviation from the protocol. Two types of protocol maps may be employed, etic and emic. In an etic protocol map the sequence of actions, contingencies and decisions are keyed into the database by a human being and represents the steps of the generalized etic protocol. Alternatively, the emic protocol map represents the sequences of actions, contingencies and decisions are inferred from previously collected data on caregiving alerts and responses. Thus the emic protocol map is derived from empirical historical data of actions taken be caregiver(s) in relation to care recipient(s) and as such is representative of the real, empirical caregiving alert, decision, response-action process whereas the etic protocol map is representative of the ideal caregiving process. This derivation uses a variety of pattern recognition and sticky function programming techniques well known to those skilled in the art. Again using the above example of protocol response to an alert indicating that a care recipient has not gotten out of bed, the etic protocol map may simply indicate that the caregiver should immediately call the care recipient and then follow the decision tree of contingencies and actions flowing from the set of 'if-then' rules entered by a person. On the other hand the emic protocol map would track each action taken by the caregiver and record its timing, sequence and, if applicable, its duration. Each time the caregiver clicks or checks an alert or action button, the system records what is done and/or each time the caregiver or another designated person enters the dwelling unit of the user/care recipient to check on their status, the system records the timing and duration of the visit using a sensor array-based behavioral monitoring. These data are then translated into a sequence of steps taken from the receipt of the alert to the end of the caregiving intervention actions which are recorded in the database for later analysis and the production of caregiving reports.

It is well known to those familiar with the practice of family and professional caregiving that it is extremely important to identify and track alerts that go unheeded and lead to no caregiving actions or inappropriate delays in response. These conditions can be routinely flagged and analyzed. In addition the more subtle problems relating to actions that are simply not the best choices can also be identified through review of case records and these flagged as well.

In the preferred embodiment of the current invention, the emic protocol serves not only to provide information for the basis of the generating care provision reports that assess the quality, quantity and efficiency of care actions for individual caregivers, individual care recipients as well as aggregate level analyses and reports, but also as the basis for sticky reminder functions enabling prompts to the caregiver along the lines of "the last three times you responded to this type of alert you took the following actions" or "the last time you called this client and there was no answer, you called Mr. Smith the next door neighbor". In this way the present decisions and course of caregiver action may be informed by past decisions and actions using elements of the emic protocol.

At the core of the inventive concept as it relates to etic and emic protocols, is the ability to compare of each particular instance of caregiving action to both the etic and emic protocol map. In this way it is possible to examine the deviance or variation from the expected (i.e., etic) behavior of the caregiver with the real (i.e., emic) behavior of the caregiver. Such variance could be coded, given numerical expression and subjected to a wide variety well known of quantitative analytical techniques. Assessment indexes could be constructed to examine the efficiency of the caregiver and/or aggregate caregiving process, such as in the simple case of the above example, the average number of minutes elapsed between an alert and the appropriate response by the appropriate person. Rule-based categorical and/or classification analyses could be conducted to assess whether or not there has been the appropriate action(s) taken and to calculate the percentage and describe the type(s) of inappropriate actions. A simple example of a rule-based comparison between etic and emic maps would query the database as to whether each of the specified caregiving actions listed in the etic protocol were empirically recorded in the course of giving care to the care recipient whether these actions were carried out in the prescribed order. A similar comparison can be executed comparing the caregiving actions to the emic protocol map to ascertain whether in what ways these actions conform and/or deviate from these baselines. Such information could prove invaluable in quality assurance and best practice analysis for caregiving in virtually all contexts.

Reporting Functionality

Since information about the caregiving process can only useful and actionable if it is received, interpreted and effectively integrated into the care provision process, the Wellbeing Record of the current invention need be presented in useable reports corresponding to a caregiving informatics template.

A caregiving informatics template is a set of information products needed to provide the appropriate feedback about the caregiving process for evaluation and quality assurance. In a general sense such a template is similar for all users. But in each particular case the template is customizable to the specific information needs of the caregiver users. The template manipulates information and provides reports on alerts, actions, outcomes or any other event required. For example, a particular template may collect and/or select information and provide reports about the amount of time passing between the sending of the alert and the responses(s) from the caregiver(s) whereas another version of the template may provide detailed information on blood pressure and weight. Templates include the capability of enabling an integration of textual care notes reporting on the changing status of the care recipient with other information sources. These care notes record the observations and assessments of caregivers and provide an additional layer of information, especially as regards the impacts and outcomes of the caregiving process on the care recipient. Since such impacts and outcomes often difficult to measure in purely quantitative terms, the qualitative narrative-based care notes information allows for a richer understanding of the quantitative data collected by other means.

In the preferred embodiment of this invention, the caregiving informatics template integrates information from behavioral, vital signs and environmental extremes monitoring to create two basic types of reports and information products: a set of Individual Wellbeing Reports focusing on the individual care recipient(s) and a set of Care Tracking Reports focusing on the performance of the caregiver(s).

The Individual Wellbeing report may contain information about remote monitoring alerts, including but not limited to type, time, duration, past history of similar alert events. The individual Wellbeing Report also contains information entered by caregivers and other persons about the status of the care recipient, including but not limited to, the observed outcomes of the actions taken in the course of caregiving. For example, if an alert indicating that the client may have fallen in their home is received by the caregiver, the report integrates this information with information gathered by the caregiver or designated individual who determines the actual status of the care recipient following the alert. In the preferred embodiment, these individual care recipient reports provide both graphical and text/narrative information on the alerts, responses and outcomes. These include an a detail page giving information on each alert set, caregiving response and outcome, a series of pages detailing the past history of alerts, responses and outcomes, and trend analytical report pages which analyze changes in caregiving actions overtime using both rule-based and trend analytical methods. Thus the individual care recipient report may provide an analysis of even subtle changes overtime with respect to alerts, non alert conditions (small changes in, for example, blood pressure or weight), changes in response actions and timing of the caregiver(s), etc. While the specific form and content of said reports may differ from one care delivery setting to another, the function of the report is to present information from a continuously updated electronic record of care for the care recipient for use in the guiding the caregiving process. This also results in a clear record of care received by the recipient, with data that can be used for quality assurance and billing purposes.

The Caregiver Tracking Report provides a series of pages presenting the number, timing and types of caregiver actions taken in relation to each individual care recipient for which the caregiver is responsible. This report may present information on a single caregiver or any group of caregivers in aggregate. In one embodiment, an aggregate view of all caregivers is presented as a "supervisory view" in which an administrator of a care delivery organization may compare the various caregivers in terms of various measures of efficiency as well as the extent to which they follow the etic protocol map in their work. Such information as non response to alerts as well as inappropriate actions can be logged, analyzed and subjected to trend analysis. Incidents of inappropriate action on the part of caregivers may be flagged and even treated as alerts, and in turn, subjected to comparative and trend analysis.

While the specifics of the form and content of the Individual Wellbeing Report and the Care Tracking Report are intended to be customizable and therefore vary from one caregiving setting to another, it is possible to give generalized examples of the preferred embodiment in terms of form, content and procedure of use.

The Individual Wellbeing Report has multiple configurations, each tailored to the information needs of the user, so that there may be one version for formal caregivers, another version for family caregivers and a third for the care recipient themselves. Typically these reports are presented graphic interface in which the first page is a "snapshot" representing the current status of monitored conditions and caregiving responses. This page is periodically updated to provide real or near real time refreshing of the information. Using graphical and textual content, the current status is represented as either "all is well" or "pay attention to" which informs the reader as to whether any immediate action may be required and also indicates the time of the information was last updated. If the "pay attention to" status is indicated, the user then clicks on a radio button to open a second report page which provides alert information about the care recipient's condition and/or the actions of caregivers. The care recipient status alerts may include but not be limited to an alert that the care recipient did not get out of bed, was unusually active through the night, is having an unexpected increase in bathroom use, has not taken their blood pressure, has had a significant weight gain, etc. The caregiver action alerts may include but not be limited to such events as caregiver(s) not checking, reading or responding to the monitoring system web, caregiver(s) not showing up at a care recipient's home for a scheduled visit, caregivers deviating from the etic or emic care protocol, etc. In addition to the alert page, several other pages of detail are available for "drill down" by the user to examine care and alert conditions history of the care recipient. These pages include textual summaries of alert activity and care delivery reports as well as trend analysis reports graphically presenting an examination of relatively subtle changes in alerts, actions and outcomes over time.

The Care Tracking Reports are intended primarily for professional care delivery organizations. They focus on the actions of specific caregivers and are intended primarily as administrative reports that serve a variety of quality assurance, accountability, supervisory and business related reporting functions. A central feature of these reports is documentation of services delivered and the determination of the need for additional services to be delivered. As such, the Care Tracking Reports provide ongoing case management level assessment useful for revising care plans, especially when this entails the provision of higher levels of support and services to the client base. While the form, content and procedure of use for this reporting system is expected to vary among different care providers, the preferred embodiment includes a first page detailing the past actions of a caregiver over the course of a reporting period (e.g., monthly, bimonthly). These actions may include but not be limited to phone calls to care recipient, home visits, meetings with family members, conferences with health and care professionals, assessment or reassessment of the care recipients' needs, adjustments and changes in the quantity and type of care delivered, etc. Additional pages of the reporting system allow for analysis of the care of any particular care recipient provided by this care giver as well as an analysis of efficiencies and deficiencies in the care actions directed at the caregiver's entire case load. Furthermore, the in preferred embodiment of the current invention, the Care Tracking Report would allow for aggregate analysis of the whole group of caregivers in terms of their productivity. These analyses may include but not be limited to the number of alerts, number and types of responses, degree of following versus deviating from the caregiving protocol(s), the number and type of changes in care plans of the caregivers' case load of care recipients, as well as the amount and type of billable services delivered to each of the client care recipients of each of the caregivers.

It will be appreciated by those skilled in the art that changes could be made to the embodiment described above without departing from the broad inventive concept thereof. It is understood, therefore, that this invention is not limited to the particular embodiments disclosed, but it is intended to cover all modifications within the spirit and scope of the present invention as defined by the appended claims.

It will be appreciated by those skilled in the art that changes could be made to the embodiment described above without departing from the broad inventive concept thereof. It is understood, therefore, that this invention is not limited to the particular embodiments disclosed, but it is intended to cover all modifications within the spirit and scope of the present invention as defined by the appended claims.

What is claimed is:

1. A method for determining the performance of a caregiver, the method being implemented in a computer that includes one or more processors, the method comprising:

monitoring, by the one or more processors, a user living area associated with a user using a first set of one or more sensors;

generating, by the one or more processors, information related to the user's need for medical care based on the monitoring;

obtaining, by the one or more processors, current caregiving information related to one or more current actions taken by a caregiver or a sequence of the one or more current actions, wherein the one or more current actions are taken by the caregiver in response to the information related to the user's need for medical care;

generating, by the one or more processors, an emic protocol based on historical caregiving information related to one or more past actions taken by the caregiver or the sequence of the one or more past actions, wherein the one or more past actions were taken by the caregiver in response to the information related to the user's need for medical care;

comparing, by the one or more processors, the current caregiving information to the emic protocol; and determining, by the one or more processors, the performance of the caregiver based on the comparison.

2. The method of claim 1, further comprising transmitting, by the one or more processors, the information related to the user's need for medical care to the caregiver, wherein the one or more current actions or the one or more historical actions comprise an acknowledgment of receipt of the transmitted information by the caregiver.

3. The method of claim 1, further comprising:

receiving, by the one or more processors, an input from the caregiver reporting an action taken by the caregiver in response to the information related to the user's need for medical care; and generating, by the one or more processors, the current caregiving information based on the input.

4. The method of claim 1, further comprising:

monitoring, by the one or more processors, the user living area for the one or more current actions or a location of the caregiver in the user living area using the first set of one or more sensors or a second set of one or more sensors; and generating, by the one or more processors, the current caregiving information based on the monitoring of the one or more current actions or the location of the caregiver in the user living area.

5. The method of claim 1, further comprising generating, by the one or more processors, a report based on the current caregiving information and the historical caregiving information.

6. The method of claim 5, further comprising generating, by the one or more processors, the report in accordance with a template.

7. The method of claim 1, further comprising:

performing, by the one or more processors, a statistical operation upon the information related to the user's need for medical care to provide a statistical determination; and determining, by the one or more processors, cognitive function information of the user in accordance with statistical determination.

8. The method of claim 1, further comprising:

detecting, by the one or more processors, one or more occurrences of a first type of behavioral activity associated with the user using at least one of the first set of one or more sensors;

generating, by the one or more processors, first behavioral activity information based on the one or more occurrences of the first type of behavioral activity;

obtaining, by the one or more processors, physiological information associated with the user using a physiological monitoring device; and generating, by the one or more processors, an integrated report based on the first behavioral activity information and the physiological information.

9. The method of claim 8, wherein the physiological information comprises body temperature, pulse rate, weight, blood sugar, blood pressure, and/or blood oxygenation associated with the user.

10. The method of claim 8, further comprising:

detecting, by the one or more processors, one or more occurrences of a second type of behavioral activity associated with the user using the at least one of the first set of one or more sensors, the second type of behavioral activity differing from the first type of behavioral activity;

generating, by the one or more processors, second behavioral activity information based on the one or more occurrences of the second type of behavioral activity; and generating, by the one or more processors, the integrated report based on the first behavioral activity information, the second behavioral activity information, and the physiological information.

11. The method of claim 8, further comprising:

generating, by the one or more processors, a request to obtain the physiological information associated with the user based on the first behavioral activity information;

obtaining, by the one or more processors, the physiological information associated with the user in response to the request using the physiological monitoring device.

12. The method of claim 1, further comprising:

generating, by the one or more processors, an alert based on the information related to the user's need for medical care; and transmitting, by the one or more processors, the alert to the caregiver.

13. The method of claim 1, further comprising:

generating, by the one or more processors, a message related to the historical caregiving information; and communicating, by the one or more processors, the message to the caregiver before the caregiver takes the one or more current actions.

14. The method of claim 1, wherein the historical caregiving information is related to one or more actions taken by a plurality of caregivers or the sequence of the one or more actions, wherein the one or more actions were taken by the plurality of caregivers in response to the information related to the user's need for medical care.

15. The method of claim 1, wherein comparing the current caregiving information to the emic protocol comprises determining, by the one or more processors, a degree of conformity and/or deviation between the current caregiving information and the emic protocol.

16. The method of claim 1, further comprising:

generating, by the one or more processors, an epic protocol based on a generalized caregiving guideline related to the information related to the user's need for medical care;

comparing, by the one or more processors, the current caregiving information to the epic protocol; and determining, by the one or more processors, the performance of the caregiver based on the comparison between the current caregiving information and the epic protocol.

17. The method of claim 16, wherein comparing the current caregiving information to the epic protocol comprises determining, by the one or more processors, a degree of conformity and/or deviation between the current caregiving information and the epic protocol.

18. The method of claim 4, wherein the caregiver is associated with a radio frequency identification (RFID) which enables the monitoring of the one or more current actions or the location of the caregiver in the user living area.

* * * * *